(12) United States Patent
Romanov et al.

(10) Patent No.: US 11,858,923 B2
(45) Date of Patent: *Jan. 2, 2024

(54) SECONDARY AMINE-SUBSTITUTED COUMARIN COMPOUNDS AND THEIR USES AS FLUORESCENT LABELS

(71) Applicant: Illumina Cambridge Limited, Cambridge (GB)

(72) Inventors: Nikolai Nikolaevich Romanov, Cambridge (GB); Patrick McCauley, Cambridge (GB); Carole Anastasi, Cambridge (GB); Xiaolin Wu, Cambridge (GB); Niall Hynes, Cambridge (GB)

(73) Assignee: Illumina Cambridge Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/856,441

(22) Filed: Jul. 1, 2022

(65) Prior Publication Data

US 2023/0025669 A1    Jan. 26, 2023

Related U.S. Application Data

(63) Continuation of application No. 16/604,964, filed as application No. PCT/GB2018/052971 on Oct. 16, 2018, now Pat. No. 11,390,619.

(30) Foreign Application Priority Data

Oct. 16, 2017   (GB) .................... 1716931

(51) Int. Cl.
| | | |
|---|---|---|
| C07D 417/04 | (2006.01) | |
| C07H 19/10 | (2006.01) | |
| C07H 19/14 | (2006.01) | |
| C12Q 1/68 | (2018.01) | |
| C07D 405/04 | (2006.01) | |
| C07D 413/04 | (2006.01) | |
| C12Q 1/6876 | (2018.01) | |

(52) U.S. Cl.
CPC ......... *C07D 417/04* (2013.01); *C07D 405/04* (2013.01); *C07D 413/04* (2013.01); *C07H 19/10* (2013.01); *C07H 19/14* (2013.01); *C12Q 1/6876* (2013.01)

(58) Field of Classification Search
CPC .. C07D 417/04; C07D 405/04; C07D 413/04; C07H 19/10; C07H 19/14; C12Q 1/6876
See application file for complete search history.

(56) References Cited

U.S. PATENT DOCUMENTS

| | | |
|---|---|---|
| 5,268,486 A | 12/1993 | Waggoner et al. |
| 5,302,509 A | 4/1994 | Cheeseman |
| 5,547,860 A | 8/1996 | Hamprecht et al. |
| 5,750,761 A | 5/1998 | Hamprecht et al. |
| 6,172,218 B1 | 1/2001 | Brenner |
| 6,465,178 B2 | 10/2002 | Chappa et al. |
| 6,924,372 B2 | 8/2005 | Czerney et al. |
| 11,390,619 B2 | 7/2022 | Romanov et al. |
| 2002/0164591 A1 | 11/2002 | Brandis |
| 2007/0020457 A1 | 1/2007 | Adefris |
| 2013/0059321 A1 | 3/2013 | Davies et al. |
| 2014/0079923 A1 | 3/2014 | George et al. |

FOREIGN PATENT DOCUMENTS

| | | |
|---|---|---|
| CN | 103740136 | 1/2016 |
| EP | 0 608 737 | 8/1994 |
| EP | 0 730 007 | 9/1996 |
| JP | 05-59111 | 3/1993 |
| JP | 05-263072 | 10/1993 |
| JP | 07-43896 | 2/1995 |
| JP | 2002-278066 | 9/2002 |
| JP | 2005-007851 | 1/2005 |
| JP | 2010-254993 | 11/2010 |
| KR | 2011-0097092 | 8/2011 |
| WO | WO 98/44151 | 10/1998 |
| WO | WO 00/06770 | 2/2000 |
| WO | WO 00/18957 | 4/2000 |
| WO | WO 00/31148 | 6/2000 |
| WO | WO 00/53812 | 9/2000 |
| WO | WO 01/01143 | 1/2001 |
| WO | WO 01/57248 | 8/2001 |
| WO | WO 02/12566 | 2/2002 |
| WO | WO 02/26891 | 4/2002 |
| WO | WO 03/014392 | 2/2003 |
| WO | WO 04/018493 | 3/2004 |
| WO | WO 04/018497 | 3/2004 |
| WO | WO 05/024010 | 3/2005 |
| WO | WO 05/047301 | 5/2005 |
| WO | WO 05/065814 | 7/2005 |
| WO | WO 06/120433 | 11/2006 |

(Continued)

OTHER PUBLICATIONS

Corrie et al., Nov.-Dec. 2000, Synthesis and fluorescence properties of substituted 7-aminocoumarin-3-carboxylate derivatives, J. Heterocyclic Chem, 37:1447-1455.

Kristoffersen et al., 2014, Testing fluorescence lifetime standards using two-photon excitation and time- domain instrumentation: rhodamine B, coumarin 6 and lucifer yellow, J. Fluoresc., 24:1015-1024.

Margulies et al., Sep. 15, 2005, Genome sequencing in microfabricated high-density picolitre reactors, Nature, 437:376-380.

Paul et al., 2013, Synthesis of new conjugated coumarin-benzimidazole hybrids and their anticancer activity, Bioorganic & Medicinal Chemistry Letters, 23(12):3667-3672.

Scheit, Nucleotide Analogs: Synthesis and Biological Function, John Wiley & Son, New York, 1980.

(Continued)

*Primary Examiner* — Jezia Riley
(74) *Attorney, Agent, or Firm* — Knobbe Martens Olson & Bear LLP

(57) ABSTRACT

The present application relates to secondary amine-substituted coumarin compounds and their uses as fluorescent labels. The compounds may be used as fluorescent labels for nucleotides in nucleic acid sequencing applications.

20 Claims, 1 Drawing Sheet

(56) References Cited

FOREIGN PATENT DOCUMENTS

| WO | WO 14/139596 | 9/2014 |
| WO | WO 16/189287 | 12/2016 |
| WO | WO 17/051201 | 3/2017 |
| WO | WO 18/060482 | 4/2018 |

OTHER PUBLICATIONS

Shendure et al., Sep. 9, 2005, Accurate multiplex polony sequencing of an evolved bacterial genome, Science, 309:1728-1732.
Srinivasan et al., Apr. 15, 1974, Anomalous fluorescence and laser emission from 7-alkylamino coumarins in acid solutions, Chemical Physics Letters, 25(4):537-540.
Ulhman et al., Jun. 1990, Antisense oligonucleotides: a new therapeutic principle, Chemical Reviews, 90(4):543-584.
Wu et al., Nov. 2009, The structure and pharmacological functions of coumarins and their derivatives, Current Medicinal Chemistry, 16(32):4236-4260.
International Search Report and Written Opinion dated Oct. 19, 2017 in application No. PCT/GB2018/052971.
Bassolino et al., 2018, Photolabile coumarins with improved efficiency through azetidinyl substitution, Chemical Science, 9:387-391.
Lavis et al., Mar. 20, 2008, Bright ideas for chemical biology, AC Chem Biol., 3(3):142-155.

SECONDARY AMINE-SUBSTITUTED COUMARIN COMPOUNDS AND THEIR USES AS FLUORESCENT LABELS

INCORPORATION BY REFERENCE TO PRIORITY APPLICATIONS

The present application is a continuation of U.S. application Ser. No. 16/604,964, filed Oct. 11, 2019, which is a U.S. national phase under 35 U.S.C. § 371 of International Application No. PCT/GB2018/052971, filed Oct. 16, 2018, which claims the benefit of priority to Great Britain Application No. 1716931.9, filed Oct. 16, 2017, each of which is incorporated by reference in its entirety.

FIELD

The present disclosure relates to secondary amine-substituted coumarin compounds and their use as fluorescent markers. In particular, the compounds may be used as fluorescent labels for nucleotides in nucleic acid sequencing applications.

BACKGROUND

Several publications and patent documents are referenced in this application to more fully describe the state of the art to which this disclosure pertains. The disclosure of each of these publications and documents is incorporated by reference herein.

Non-radioactive detection of nucleic acids bearing fluorescent labels is an important technology in molecular biology. Many procedures employed in recombinant DNA technology previously relied on the use of nucleotides or polynucleotides radioactively labeled with, for example $^{32}P$. Radioactive compounds permit sensitive detection of nucleic acids and other molecules of interest. However, there are serious limitations in the use of radioactive isotopes such as their expense, limited shelf life, insufficient sensitivity, and, more importantly, safety considerations. Eliminating the need for radioactive labels reduces both the safety risks and the environmental impact and costs associated with, for example, reagent disposal. Methods amenable to non-radioactive fluorescent detection include by way of non-limiting examples, automated DNA sequencing, hybridization methods, real-time detection of polymerase-chain-reaction products, and immunoassays.

For many applications, it is desirable to employ multiple spectrally-distinguishable fluorescent labels to achieve independent detection of a plurality of spatially-overlapping analytes. In such multiplex methods, the number of reaction vessels may be reduced, simplifying experimental protocols and facilitating the production of application-specific reagent kits. In multi-color automated DNA sequencing systems for example, multiplex fluorescent detection allows for the analysis of multiple nucleotide bases in a single electrophoresis lane, thereby increasing throughput over single-color methods, and reducing uncertainties associated with inter-lane electrophoretic mobility variations.

However, multiplex fluorescent detection can be problematic and there are a number of important factors that constrain selection of appropriate fluorescent labels. First, it may be difficult to find dye compounds with suitably-resolved absorption and emission spectra in a given application. In addition, when several fluorescent dyes are used together, generating fluorescence signals in distinguishable spectral regions by simultaneous excitation may be complicated because absorption bands of the dyes are usually widely separated, so it is difficult to achieve comparable fluorescence excitation efficiencies even for two dyes. Many excitation methods use high power light sources like lasers and therefore the dye must have sufficient photo-stability to withstand such excitation. A final consideration of particular importance to molecular biology methods is the extent to which the fluorescent dyes must be compatible with reagent chemistries such as, for example, DNA synthesis solvents and reagents, buffers, polymerase enzymes, and ligase enzymes.

As sequencing technology advances, a need has developed for further fluorescent dye compounds, their nucleic acid conjugates, and multiple dye sets that satisfy all the above constraints and that are amenable particularly to high throughput molecular methods such as solid phase sequencing and the like.

Fluorescent dye molecules with improved fluorescence properties such as suitable fluorescence intensity, shape, and wavelength maximum of fluorescence can improve the speed and accuracy of nucleic acid sequencing. Strong fluorescence signals are especially important when measurements are made in water-based biological buffers and at higher temperatures as the fluorescence intensities of most dyes are significantly lower under such conditions. Moreover, the nature of the base to which a dye is attached also affects the fluorescence maximum, fluorescence intensity, and others spectral dye properties. The sequence-specific interactions between the nucleobases and the fluorescent dyes can be tailored by specific design of the fluorescent dyes. Optimization of the structure of the fluorescent dyes can improve the efficiency of nucleotide incorporation, reduce the level of sequencing errors, and decrease the usage of reagents in, and therefore the costs of, nucleic acid sequencing.

Some optical and technical developments have already led to greatly improved image quality but were ultimately limited by poor optical resolution. Generally, optical resolution of light microscopy is limited to objects spaced at approximately half of the wavelength of the light used. In practical terms, then, only objects that are laying quite far apart (at least 200 to 350 nm) could be resolved by light microscopy. One way to improve image resolution and increase the number of resolvable objects per unit of surface area is to use excitation light of a shorter wavelength. For example, if light wavelength is shortened by $\Delta\lambda \sim 100$ nm with the same optics, resolution will be better (about $\Delta$ 50 nm/(about 15%)), less-distorted images will be recorded, and the density of objects on the recognizable area will be increased about 35%.

Certain nucleic acid sequencing methods employ laser light to excite and detect dye-labeled nucleotides. These instruments use longer wavelength light, such as red lasers, along with appropriate dyes that are excitable at 660 nm. To detect more densely packed nucleic acid sequencing clusters while maintaining useful resolution, a shorter wavelength blue light source (450-460 nm) may be used. In this case, optical resolution will be limited not by the emission wavelength of the longer wavelength red fluorescent dyes but rather by the emission of dyes excitable by the next longest wavelength light source, for example, by "green laser" at 532 nm. Thus, there is a need for blue dye labels for use in fluorescence detection in sequencing applications.

Although blue-dye chemistry and associated laser technologies have improved, for example, to yield dyes for DVD and Blu-ray disks, these compounds are not appropriate for bio-labeling and cannot be used as biomarkers.

Unfortunately, commercially available blue dyes with strong fluorescence suitable for nucleotide labeling are still quite rare. Described herein are new fluorescent compounds suitable for nucleotide labeling with strong fluorescence under blue light excitation.

SUMMARY

The present invention relates to secondary amine-substituted coumarin derivatives. The compounds may be useful as fluorescent labels, particularly for nucleotide labeling in nucleic acid sequencing applications. In some aspects, the dyes absorb light optimally at a wavelength of 450-460 nm and are particularly advantageous in situations where blue wavelength excitation sources having a wavelength of 450-460 nm are used. Blue wavelength excitation allows detection and resolution of a higher density of features per unit area due to the shorter wavelength of fluorescence emission. When such dyes are used in conjugates with nucleotides, improvements can be seen in the length, intensity, accuracy, and quality of sequencing reads obtained during nucleic acid sequencing methods.

In a first aspect are compounds of Formula (I) or salts thereof:

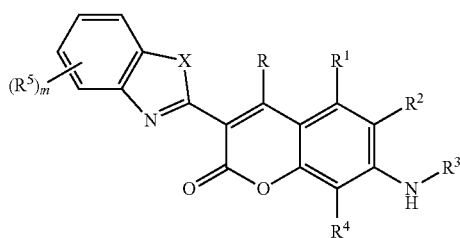

(I)

wherein:
X is O, S, Se, or NR″, where R″ is H or $C_{1-6}$alkyl;
R and $R^1$ are each independently H, halo, —CN, —$CO_2H$, amino, —OH, C-amido, N-amido, —$NO_2$, —$SO_3H$, —$SO_2NH_2$, optionally substituted alkyl, optionally substituted alkenyl, optionally substituted alkynyl, optionally substituted alkoxy, optionally substituted aminoalkyl, optionally substituted carbocyclyl, optionally substituted heterocyclyl, optionally substituted aryl, or optionally substituted heteroaryl;
$R^2$ and $R^4$ are each independently H, halo, —CN, —$CO_2H$, amino, —OH, C-amido, N-amido, —$NO_2$, —$SO_3H$, —$SO_2NH_2$, optionally substituted alkyl, optionally substituted alkenyl, optionally substituted alkynyl, optionally substituted alkoxy, optionally substituted aminoalkyl, optionally substituted carbocyclyl, optionally substituted heterocyclyl, optionally substituted aryl, or optionally substituted heteroaryl; or one of $R^2$ and $R^4$ is linked to $R^3$ to form an optionally substituted heterocyclic ring;
$R^3$ is H, $C_{1-6}$alkyl, substituted $C_{2-6}$alkyl, optionally substituted $C_{2-6}$alkenyl, optionally substituted $C_{2-6}$alkynyl, or optionally substituted carbocyclyl, heterocyclyl, aryl, or heteroaryl, or $R^3$ is linked to $R^2$ or $R^4$ to form an optionally substituted ring;
wherein when R is —CN, $R^3$ is not $C_{1-6}$alkyl;
each $R^5$ is independently halo, —CN, —$CO_2H$, amino, —OH, C-amido, N-amido, —$NO_2$, —$SO_3H$, —$SO_2NH_2$, optionally substituted alkyl, optionally substituted alkenyl, optionally substituted alkynyl, optionally substituted alkoxy, optionally substituted aminoalkyl, optionally substituted carbocyclyl, optionally substituted heterocyclyl, optionally substituted aryl, or optionally substituted heteroaryl; and
m is 0, 1, 2, 3, or 4.

In some aspects, R is not —CN, such that R is H, halo, —$CO_2H$, amino, —OH, C-amido, N-amido, —$NO_2$, —$SO_3H$, —$SO_2NH_2$, optionally substituted alkyl, optionally substituted alkenyl, optionally substituted alkynyl, optionally substituted alkoxy, optionally substituted aminoalkyl, optionally substituted carbocyclyl, optionally substituted heterocyclyl, optionally substituted aryl, or optionally substituted heteroaryl.

In another aspect is a compound of Formula (II) or a salt thereof:

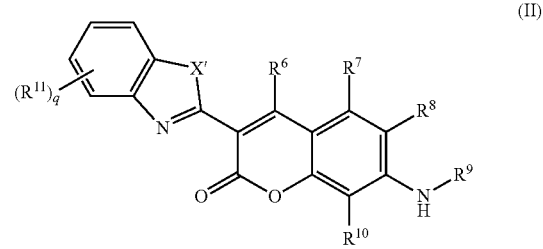

(II)

wherein:
X′ is selected from O, S, and $NR^p$, where $R^p$ is H or $C_{1-6}$ alkyl;
$R^6$ is H or $C_{1-4}$ alkyl;
$R^7$ is H, halo, —CN, —OH, optionally substituted $C_{1-4}$alkyl, optionally substituted $C_{1-4}$alkenyl, optionally substituted $C_{2-4}$alkynyl, —$CO_2H$, —$SO_3H$, —$SO_2NH_2$, —$SO_2NH(C_{1-4}alkyl)$, —$SO_2N(C_{1-4}alkyl)_2$, and optionally substituted $C_{1-4}$ alkoxy;
$R^8$ and $R^{10}$ are each independently H, halo, —CN, —$CO_2H$, amino, —OH, —$SO_3H$, —$SO_2NH_2$, —$SO_2NH(C_{1-4}$ alkyl), —$SO_2N(C_{1-4}$ alkyl)$_2$, optionally substituted $C_{1-6}$ alkyl, optionally substituted $C_{1-6}$alkenyl, optionally substituted $C_{2-6}$alkynyl, or optionally substituted $C_{1-6}$alkoxy; or
one of $R^8$ and $R^{10}$ is H, halo, —CN, —$CO_2H$, amino, —OH, —$SO_3H$, —$SO_2NH_2$, —$SO_2NH(C_{1-4}$ alkyl), —$SO_2N(C_{1-4}alkyl)_2$, optionally substituted $C_{1-6}$alkyl, optionally substituted $C_{1-6}$alkenyl, optionally substituted $C_{2-6}$alkynyl, or optionally substituted $C_{1-6}$alkoxy, and the other of $R^8$ and $R^{10}$ is taken with $R^9$ to form an optionally substituted 4- to 7-membered heterocyclic ring;
$R^9$ is $C_{2-6}$alkyl or $C_{1-6}$alkyl substituted with —$CO_2H$, —$CO_2C_{1-4}$alkyl, —$CONH_2$, —$CONH(C_{1-4}alkyl)$, —$CON(C_{1-4}$ alkyl)$_2$, —CN, —$SO_3H$, —$SO_2NH_2$, —$SO_2NH(C_{1-4}$ alkyl), or —$SO_2N(C_{1-4}$ alkyl)$_2$;
each $R^{11}$ is independently halo, —CN, carboxy, amino, —OH, C-amido, N-amido, nitro, —$SO_3H$, —$SO_2NH_2$, —$SO_2NH(C_{1-4}alkyl)$, —$SO_2N(C_{1-4}alkyl)_2$, optionally substituted alkyl, optionally substituted alkenyl, optionally substituted alkynyl, and optionally substituted $C_{1-6}$ alkoxy; and
q is 0, 1, or 2.

In another embodiment, a compound of the present disclosure is conjugated with a substrate moiety such as, for example, a nucleoside, nucleotide, polynucleotide, polypeptide, carbohydrate, ligand, particle, cell, semi-solid surface (e.g., gel), or solid surface. The conjugation can be carried out via a carboxyl group —$CO_2H$, which can be reacted using methods known in the art with an amino or hydroxyl group on a moiety (such as a nucleotide) or a linker bound thereto, to form an amide or ester.

According to a further aspect of the disclosure therefore, there are provided dye compounds comprising linker groups to enable, for example, covalent attachment to a substrate moiety. Linking may be carried out at any position of the dye, including at any of the R groups. Linking may be carried out via $R^3$ or via $R^5$ of Formula (I), or via $R^9$ or $R^{11}$ of Formula (II).

According to a further aspect the disclosure provides a nucleoside or nucleotide compound defined by the formula:

N-L-Dye wherein N is a nucleotide;
L is an optional linker moiety; and
Dye is a fluorescent compound according to the present disclosure.

Thus, some embodiments described herein are related to a moiety, in particular nucleotide or oligonucleotide, labeled with a compound of (a) Formula (I) or (b) Formula (II).

In a further aspect the disclosure provides methods of sequencing using the dye compounds of the present disclosure.

According to a further aspect the disclosure also provides a kit comprising a dye compound (free or in conjugate form) that may be used in various immunological assays, oligonucleotide or nucleic acid labeling, or for DNA sequencing by synthesis. In yet another aspect, the disclosure provides kits comprising dye "sets" particularly suited to cycles of sequencing by synthesis on an automated instrument platform. In some aspects are kits containing one or more nucleotides where at least one nucleotide is a labeled nucleotide described herein.

A further aspect of the disclosure is the chemical preparation of compounds of the disclosure, including secondary amine-substituted coumarin dyes and moieties such as nucleotides labeled with such dyes.

In further aspects are methods of sequencing including incorporating a labeled nucleotide described herein in a polynucleotide in a sequencing assay, and detecting the incorporated, labeled nucleotide.

DETAILED DESCRIPTION

Figure 1A:
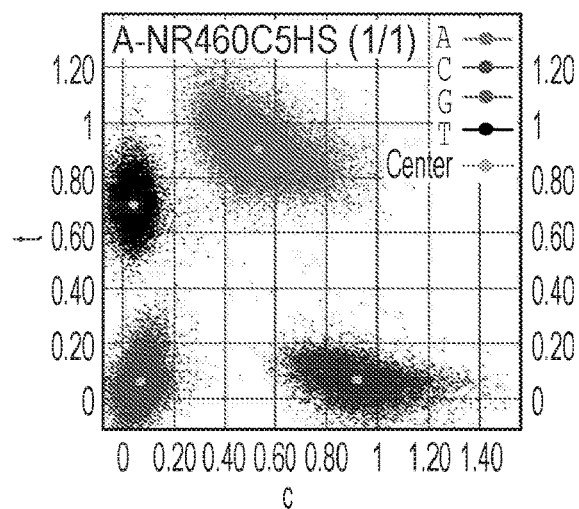
FIGS. 1A, 1B, and 1C are scatter plots that show hypothetical sequencing results for three blue dyes as described herein using Illumina sequencing-by-synthesis (SBS) chemistry. The dyes on the four nucleotides were detected as four distinct, spectrally resolved areas, as described in Example 5.

This disclosure provides secondary amine-substituted coumarin compounds particularly suitable for methods of fluorescence detection and sequencing by synthesis. Embodiments described herein relate to dyes and their derivatives of the structure of Formula (I).

According to a first aspect the disclosure provides compounds of Formula (I) or salts thereof.

Particular limitations for the various substituents are shown below. Each single group can be combined with any other individual limitation unless otherwise specified.

To improve fluorescent properties of the biomarkers and especially their bioconjugates in water-based solutions, the compound of Formula (I) is a compound in which:
i) $R^2$ is —$SO_3H$; and/or
ii) $R^4$ is —$SO_3H$; and/or
iii) $R^5$ is —$SO_3H$ or —$SO_2NH_2$.

In some aspects, X is O or S. In some aspects, X is O. In some aspects, X is S. In some aspects, X is NR″, where R″ is H or $C_{1-6}$ alkyl, and in some aspects, R″ is H.

In some aspects, $R^3$ is H. In some aspects, $R^3$ is methyl, ethyl, propyl, isopropyl, butyl, isobutyl, sec-butyl, tert-butyl, pentyl, or hexyl. In other aspects, $R^3$ is ethyl. In other aspects, $R^3$ is substituted $C_{2-6}$ alkyl. In other aspects, $R^3$ is $C_{2-6}$ alkyl substituted with —$CO_2H$. In other aspects, $R^3$ is optionally substituted $C_{2-6}$alkenyl or optionally substituted $C_{2-6}$alkynyl. In some aspects, $R^3$ is linked to $R^2$ or $R^4$ to form an optionally substituted ring.

Where coupling to a linker or nucleotide is via $R^3$, $R^3$ should be of sufficient length to allow coupling to a functional group attached thereto. In some aspects, $R^3$ is not —$CH_2COOH$ or —$CH_2COO^-$.

Optionally, $R^3$ is —$(CH_2)_nCOOH$ where n is 2-6. In some aspects, n is 2, 3, 4, 5 or 6. In other aspects, n is 2 or 5. In some aspects, n is 2. In some aspects, n is 5.

Optionally, $R^3$ is —$(CH_2)_nSO_3H$ where n is 2-6. In some aspects, n is 2, 3, 4, 5 or 6. In other aspects, n is 2 or 5. In some aspects, n is 2. In some aspects, n is 5.

The benzene ring of the indole moiety is optionally substituted in any one, two, three, or four positions by a substituent shown as $R^5$. Where m is zero, the benzene ring is unsubstituted. Where m is greater than 1, each $R^5$ may be the same or different. In some aspects, m is 0. In other aspects, m is 1. In other aspects, m is 2. In some aspects, m is 1, 2, or 3, and each $R^5$ is independently halo, —CN, —$CO_2H$, amino, —OH, —$SO_3H$, or —$SO_2NH_2$. In some aspects, $R^5$ is —$(CH_2)_xCOOH$ where x is 2-6. In some aspects, x is 2, 3, 4, 5 or 6. In other aspects, x is 2 or 5. In some aspects, x is 2. In some aspects, x is 5.

In some aspects, $R^5$ is halo, —CN, —$CO_2H$, —$SO_3H$, —$SO_2NH_2$, or optionally substituted $C_{1-6}$alkyl. In some aspects, $R^5$ is halo, —$CO_2H$, —$SO_3H$, or —$SO_2NH_2$. In some aspects, $R^5$ is $C_{2-6}$alkyl substituted with —$CO_2H$, —$SO_3H$, or —$SO_2NH_2$. In some aspects, each $R^5$ is independently optionally substituted $C_{1-6}$ alkyl, halo, —CN, —$CO_2H$, amino, —OH, —$SO_3H$, or —$SO_2NH_2$.

In some aspects, $R^1$ is H. In some aspects, $R^1$ is halo. In some aspects, $R^1$ is Cl. In some aspects, $R^1$ is $C_{1-6}$ alkyl. In some aspects, $R^1$ is methyl.

In some aspects, R is H. In some aspects, R is halo. In some aspects, R is Cl. In some aspects, R is $C_{1-6}$alkyl. In some aspects, R is methyl. In some aspects, R is not —CN. In some aspects, R is H, halo, —$CO_2H$, amino, —OH, C-amido, N-amido, —$NO_2$, —$SO_3H$, —$SO_2NH_2$, optionally substituted alkyl, optionally substituted alkenyl, optionally substituted alkynyl, optionally substituted alkoxy, optionally substituted aminoalkyl, optionally substituted carbocyclyl, optionally substituted heterocyclyl, optionally substituted aryl, or optionally substituted heteroaryl.

In some aspects, $R^2$ is H. In some aspects, $R^2$ is optionally substituted alkyl. In some aspects, $R^2$ is $C_{1-4}$alkyl optionally substituted with —$CO_2H$ or —$SO_3H$. In some aspects, $R^2$ is —$SO_3H$. In some aspects, $R^2$ is linked to $R^3$ to form an optionally substituted heterocyclic ring, such as a pyrrolidine or piperidine, optionally substituted with one or more alkyl groups. In some aspects, $R^2$ is H, optionally substituted alkyl, $C_{1-4}$ alkyl optionally substituted with —$CO_2H$ or —$SO_3H$, or —$SO_3H$. In some aspects, $R^2$ is H or —$SO_3H$.

In some aspects, $R^4$ is H. In some aspects, $R^4$ is optionally substituted alkyl. In some aspects, $R^4$ is $C_{1-4}$alkyl optionally substituted with —$CO_2H$ or —$SO_3H$. In some aspects, $R^4$ is —$SO_3H$. In some aspects, $R^4$ is linked to $R^3$ to form an optionally substituted heterocyclic ring, such as a pyrrolidine or piperidine, optionally substituted with one or more alkyl groups.

Particular examples of a compound of Formula (I) include where X is O or S; R is H; $R^1$ is H; $R^3$ is —$(CH_2)_nCOOH$ where n is 2-6; $R^5$ is H, —$SO_3H$, or —$SO_2NH_2$; $R^2$ is H or —$SO_3H$; and $R^4$ is H or —$SO_3H$.

Particular examples of a compound of Formula (I) include where X is O or S; R is H; $R^1$ is H; $R^3$ is —$(CH_2)_2COOH$; $R^5$ is H, —$SO_3H$, or —$SO_2NH_2$; $R^2$ is H or —$SO_3H$; and $R^4$ is H or —$SO_3H$.

Particular examples of a compound of Formula (I) include where X is O or S; R is H; $R^1$ is H; $R^3$ is —$(CH_2)_5COOH$; $R^5$ is H, —$SO_3H$, or —$SO_2NH_2$; $R^2$ is H or —$SO_3H$; and $R^4$ is H or —$SO_3H$.

In some aspects of Formula (II), X' is O. In some aspects, X' is S. In some aspects, X' is $NR^p$, where $R^p$ is H or $C_{1-6}$alkyl. In some aspects, X' is $NR^p$, where $R^p$ is H.

In some aspects, $R^6$ is H. In some aspects, $R^6$ is $C_{1-4}$ alkyl.

In some aspects, $R^7$ is H. In some aspects, $R^7$ is optionally substituted $C_{1-4}$ alkyl, —$CO_2H$, —$SO_3H$, —$SO_2NH_2$, —$SO_2NH(C_{1-4}$ alkyl), or —$SO_2N(C_{1-4}$ alkyl$)_2$. In some aspects, $R^7$ is $C_{1-4}$ alkyl optionally substituted with —$CO_2H$.

In some aspects, $R^8$ is H. In some aspects, $R^8$ is —$CO_2H$, —$SO_3H$, or —$SO_2NH_2$. In some aspects, $R^8$ is —$SO_3H$.

In some aspects, $R^{10}$ is H. In some aspects, $R^{10}$ is —$CO_2H$, —$SO_3H$, or —$SO_2NH_2$. In some aspects, $R^{10}$ is —$SO_3H$. In some aspects, $R^8$ is H and $R^{10}$ is —$SO_3H$. In some aspects, $R^8$ is —$SO_3H$ and $R^{10}$ is H.

In some aspects, one of $R^8$ and $R^{10}$ is H, halo, —CN, —$CO_2H$, amino, —OH, —$SO_3H$, —$SO_2NH_2$, —$SO_2NH(C_{1-4}$ alkyl), —$SO_2N(C_{1-4}$ alkyl$)_2$, optionally substituted $C_{1-6}$alkyl, optionally substituted $C_{1-6}$alkenyl, optionally substituted $C_{2-6}$alkynyl, or optionally substituted $C_{1-6}$alkoxy, and the other of $R^8$ and $R^{10}$ is taken with $R^9$ to form an optionally substituted 4- to 7-membered heterocyclic ring.

In some aspects, $R^9$ is $C_{2-6}$ alkyl. In some aspects, $R^9$ is $C_{1-6}$ alkyl substituted with —$CO_2H$, —$CO_2C_{1-4}$ alkyl, —$CONH_2$, —$CONH(C_{1-4}$ alkyl), —$CON(C_{1-4}$ alkyl$)_2$, —CN, —$SO_3H$, —$SO_2NH_2$, —$SO_2NH(C_{1-4}$ alkyl), or —$SO_2N(C_{1-4}$ alkyl$)_2$. In some aspects, $R^9$ is $C_{1-6}$ alkyl substituted with —$CO_2H$. In some aspects, $R^9$ is —$(CH_2)_y$—$CO_2H$, where y is 2, 3, 4, or 5.

In some aspects, each $R^{11}$ is independently halo, —$CO_2H$, —$SO_3H$, —$SO_2NH_2$, —$SO_2NH(C_{1-4}$alkyl), —$SO_2N(C_{1-4}$ alkyl$)_2$, or optionally substituted alkyl. In other aspects, each $R^{11}$ is independently halo, —$CO_2H$, —$SO_3H$, or —$SO_2NH_2$.

In some aspects, q is 0. In other aspects, q is 1. In still other aspects, q is 2.

Specific examples of secondary amine-substituted coumarin dyes include:

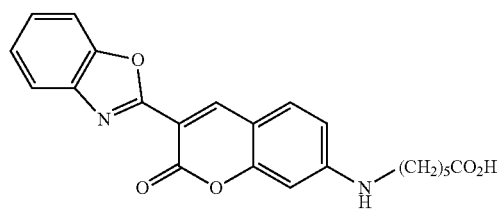

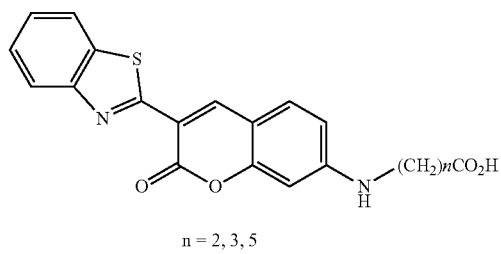

n = 2, 3, 5

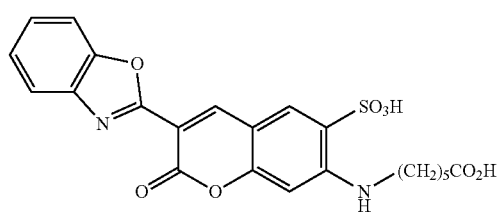

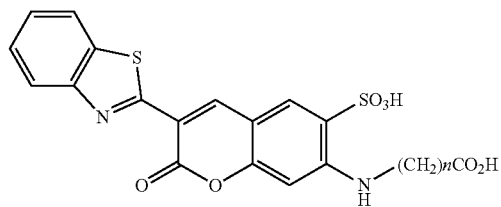

n = 2, 5

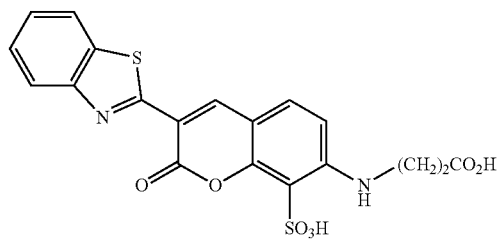

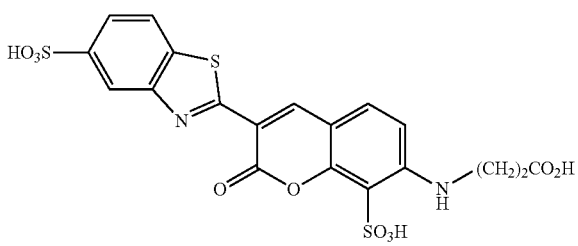

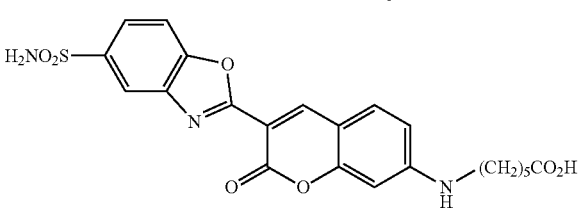

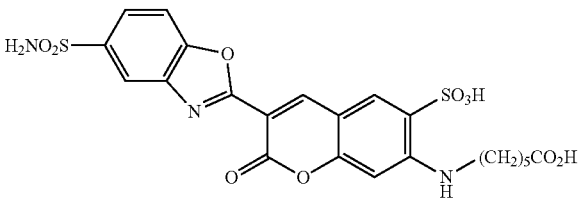

-continued

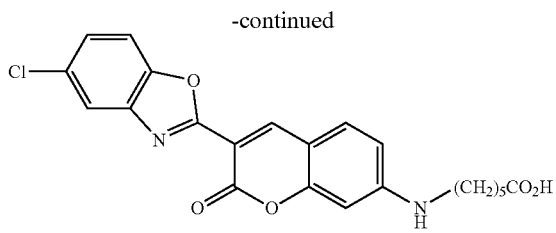

and salts thereof.

A particularly useful compound is a nucleotide or oligonucleotide labeled with a dye as described herein. The labeled nucleotide or oligonucleotide may have the label attached to the nitrogen atom of coumarin molecule via an alkyl-carboxy group to form an alkyl-amide. The labeled nucleotide or oligonucleotide may have the label attached to the C5 position of a pyrimidine base or the C7 position of a 7-deaza purine base through a linker moiety.

The labeled nucleotide or oligonucleotide may also have a blocking group covalently attached to the ribose or deoxyribose sugar of the nucleotide. The blocking group may be attached at any position on the ribose or deoxyribose sugar. In particular embodiments, the blocking group is at the 3' OH position of the ribose or deoxyribose sugar of the nucleotide.

Provided herein are kits including two or more nucleotides wherein at least one nucleotide is a nucleotide labeled with a compound of the present disclosure. The kit may include two or more labeled nucleotides. The nucleotides may be labeled with two or more fluorescent labels. Two or more of the labels may be excited using a single excitation source, which may be a laser. For example, the excitation bands for the two or more labels may be at least partially overlapping such that excitation in the overlap region of the spectrum causes both labels to emit fluorescence. In particular embodiments, the emission from the two or more labels will occur in different regions of the spectrum such that presence of at least one of the labels can be determined by optically distinguishing the emission.

The kit may contain four labeled nucleotides, where the first of four nucleotides is labeled with a compound as disclosed herein. In such a kit, each of the four nucleotides can be labeled with a compound that is the same or different from the label on the other three nucleotides. Thus, one or more of the compounds can have a distinct absorbance maximum and/or emission maximum such that the compound(s) is(are) distinguishable from other compounds. For example, each compound can have a distinct absorbance maximum and/or emission maximum such that each of the compounds is distinguishable from the other three compounds. It will be understood that parts of the absorbance spectrum and/or emission spectrum other than the maxima can differ and these differences can be exploited to distinguish the compounds. The kit may be such that two or more of the compounds have a distinct absorbance maximum. The compounds of the invention typically absorb light in the region below 500 nm.

The compounds, nucleotides, or kits that are set forth herein may be used to detect, measure, or identify a biological system (including, for example, processes or components thereof). Exemplary techniques that can employ the compounds, nucleotides or kits include sequencing, expression analysis, hybridization analysis, genetic analysis, RNA analysis, cellular assay (e.g., cell binding or cell function analysis), or protein assay (e.g., protein binding assay or protein activity assay). The use may be on an automated instrument for carrying out a particular technique, such as an automated sequencing instrument. The sequencing instrument may contain two lasers operating at different wavelengths.

Disclosed herein are methods of synthesizing compounds of the disclosure. Dyes according to the present disclosure may be synthesized from a variety of different suitable starting materials. Methods for preparing coumarin dyes are well known in the art.

Definitions

The section headings used herein are for organizational purposes only and are not to be construed as limiting the subject matter described.

It is noted that, as used in this specification and the appended claims, the singular forms "a", "an" and "the" include plural referents unless expressly and unequivocally limited to one referent. It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps but may include additional steps. When used in the context of a compound, composition, or device, the term "comprising" means that the compound, composition, or device includes at least the recited features or components, but may also include additional features or components.

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 6 carbon atoms. The alkyl group may be designated as "$C_{1-4}$alkyl" or similar designations. By way of example only, "$C_{1-6}$alkyl" indicates that there are one to six carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 6 carbon atoms. The alkenyl group may be designated as "$C_{2-6}$ alkenyl" or similar designations. By way of example only, "$C_{2-6}$alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 6 carbon atoms. The alkynyl group may be designated as "$C_{2-6}$ alkynyl" or similar designations. By way of example only, "$C_{2-6}$alkynyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 6 carbon atoms. The heteroalkyl group may be designated as "$C_{1-6}$ heteroalkyl" or similar designations. The heteroalkyl group may contain one or more heteroatoms. By way of example only, "$C_{4-6}$heteroalkyl" indicates that there are four to six carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-6}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinolinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-6}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

As used herein, "cycloalkyl" means a fully saturated carbocyclyl ring or ring system. Examples include cyclopropyl, cyclobutyl, cyclopentyl, and cyclohexyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidinonyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

An "O-carboxy" group refers to a "—OC(═O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "C-carboxy" group refers to a "—C(═O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes carboxyl (i.e., —C(═O)OH).

A "sulfonyl" group refers to an "—$SO_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "sulfino" group refers to a "—S(═O)OH" group.

An "S-sulfonamido" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-sulfonamido" group refers to a "—$N(R_A)SO_2R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "C-amido" group refers to a "—C(═O)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-amido" group refers to a "—$N(R_A)$C(═O)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes free amino (i.e., —$NH_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, —CN, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, —$SO_3H$, sulfino, —$OSO_2C_{1-4}$alkyl, and oxo (═O). Wherever a group is described as "optionally substituted" that group can be substituted with the above substituents.

In some embodiments, substituted alkyl, alkenyl, or alkynyl groups are substituted with one or more substituents selected from the group consisting of halo, —CN, $SO_3^-$, SR$^a$, OR$^a$, NR$^b$R$^c$, oxo, CONR$^b$R$^c$, COOH, and COOR$^b$, where R$^a$, R$^b$ and R$^c$ are each independently selected from H, alkyl, substituted alkyl, alkenyl, substituted alkenyl, alkynyl, substituted alkynyl, aryl, and substituted aryl.

Compounds described herein can be represented as several mesomeric forms. Where a single structure is drawn, any of the relevant mesomeric forms are intended. The coumarin compounds described herein are represented by a single structure but can equally be shown as any of the related mesomeric forms. Exemplary mesomeric structures are shown below for Formula (I):

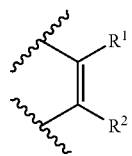

and R$^1$ and R$^2$ are defined as selected from the group consisting of hydrogen and alkyl, or R$^1$ and R$^2$ together with (I)

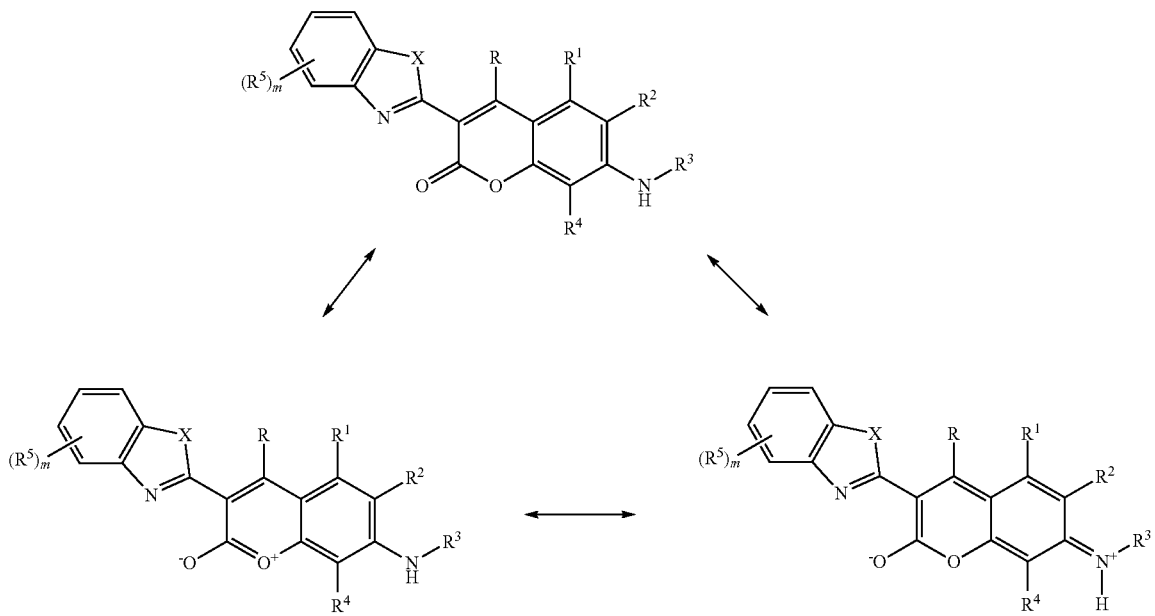

In each instance where a single mesomeric form of a compound described herein is shown, the alternative mesomeric forms are equally contemplated.

As understood by one of ordinary skill in the art, a compound described herein may exist in ionized form, e.g., —CO$_2^-$ or —SO$_3^-$. If a compound contains a positively or negatively charged substituent group, for example, SO$_3^-$, it may also contain a negatively or positively charged counterion such that the compound as a whole is neutral. In other aspects, the compound may exist in a salt form, where the counterion is provided by a conjugate acid or base.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene" or "alkenylene."

When two "adjacent" R groups are said to form a ring "together with the atom to which they are attached," it is meant that the collective unit of the atoms, intervening bonds, and the two R groups are the recited ring. For example, when the following substructure is present:

the atoms to which they are attached form an aryl or carbocyclyl, it is meant that R$^1$ and R$^2$ can be selected from hydrogen or alkyl, or alternatively, the substructure has structure:

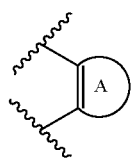

where A is an aryl ring or a carbocyclyl containing the depicted double bond.

Labeled Nucleotides

According to an aspect of the disclosure, there are provided dye compounds suitable for attachment to substrate moieties, particularly comprising linker groups to enable attachment to substrate moieties. Substrate moieties can be virtually any molecule or substance to which the dyes of the disclosure can be conjugated, and, by way of non-limiting example, may include nucleosides, nucleotides, polynucleotides, carbohydrates, ligands, particles, solid surfaces, organic and inorganic polymers, chromosomes, nuclei, living cells, and combinations or assemblages thereof. The dyes can be conjugated by an optional linker by a variety of means including hydrophobic attraction, ionic attraction, and covalent attachment. In some aspects, the dyes are conjugated to the substrate by covalent attachment. More particularly, the covalent attachment is by means of a linker group. In some instances, such labeled nucleotides are also referred to as "modified nucleotides."

The present disclosure further provides conjugates of nucleosides and nucleotides labeled with one or more of the dyes set forth herein (modified nucleotides). Labeled nucleosides and nucleotides are useful for labeling polynucleotides formed by enzymatic synthesis, such as, by way of non-limiting example, in PCR amplification, isothermal amplification, solid phase amplification, polynucleotide sequencing (e.g., solid phase sequencing), nick translation reactions and the like.

The attachment to the biomolecules may be via the R, $R^1$, $R^2$, $R^3$, $R^4$, $R^5$, or X position of the compound of Formula (I). In some aspects, the connection is via the $R^3$ or $R^5$ group of Formula (I). For Formula (II), attachment may be at any position $R^{6-11}$ or X'. In some embodiments, the substituent group is a substituted alkyl, for example, alkyl substituted with —$CO_2H$ or an activated form of carboxyl group, for example, an amide or ester, which may be used for attachment to the amino or hydroxyl group of the biomolecules. In one embodiment, the R, $R^1$, $R^2$, $R^3$, $R^4$, $R^5$, or X group of Formula (I) or the $R^{6-11}$ or X' groups of Formula (II) may contain an activated ester or amide residue most suitable for further amide/peptide bond formation. The term "activated ester" as used herein, refers to a carboxyl group derivative which is capable of reacting in mild conditions, for example, with a compound containing an amino group. Non-limiting examples of activated esters include but not limited to p-nitrophenyl, pentafluorophenyl and succinimido esters.

In some embodiments, the dye compounds may be covalently attached to oligonucleotides or nucleotides via the nucleotide base. For example, the labeled nucleotide or oligonucleotide may have the label attached to the C5 position of a pyrimidine base or the C7 position of a 7-deaza purine base through a linker moiety. The labeled nucleotide or oligonucleotide may also have a 3'-OH blocking group covalently attached to the ribose or deoxyribose sugar of the nucleotide.

A particular useful application of the new fluorescent dyes as described herein is for labeling biomolecules, for example, nucleotides or oligonucleotides. Some embodiments of the present application are directed to a nucleotide or oligonucleotide labeled with the new fluorescent compounds as described herein.

Linkers

The dye compounds as disclosed herein may include a reactive linker group at one of the substituent positions for covalent attachment of the compound to a substrate or another molecule. Reactive linking groups are moieties capable of forming a bond (e.g., a covalent or non-covalent bond), in particular a covalent bond. In a particular embodiment the linker may be a cleavable linker. Use of the term "cleavable linker" is not meant to imply that the whole linker is required to be removed. The cleavage site can be located at a position on the linker that ensures that part of the linker remains attached to the dye and/or substrate moiety after cleavage. Cleavable linkers may be, by way of non-limiting example, electrophilically cleavable linkers, nucleophilically cleavable linkers, photocleavable linkers, cleavable under reductive conditions (for example disulfide or azide containing linkers), oxidative conditions, cleavable via use of safety-catch linkers and cleavable by elimination mechanisms. The use of a cleavable linker to attach the dye compound to a substrate moiety ensures that the label can, if required, be removed after detection, avoiding any interfering signal in downstream steps.

Useful linker groups may be found in PCT Publication No. WO2004/018493 (herein incorporated by reference), examples of which include linkers that may be cleaved using water-soluble phosphines or water-soluble transition metal catalysts formed from a transition metal and at least partially water-soluble ligands. In aqueous solution the latter form at least partially water-soluble transition metal complexes. Such cleavable linkers can be used to connect bases of nucleotides to labels such as the dyes set forth herein.

Particular linkers include those disclosed in PCT Publication No. WO2004/018493 (herein incorporated by reference) such as those that include moieties of the formulae:

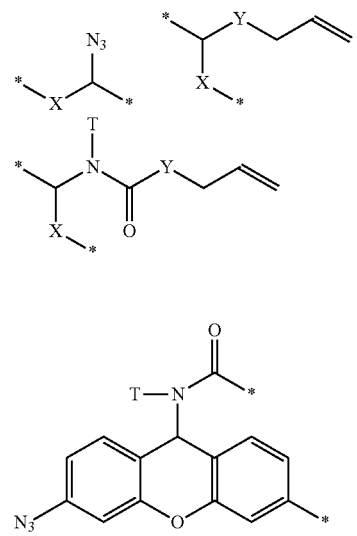

(wherein X is selected from the group comprising O, S, NH and NQ wherein Q is a C1-10 substituted or unsubstituted alkyl group, Y is selected from the group comprising O, S, NH and N(allyl), T is hydrogen or a $C_1$-$C_{10}$ substituted or unsubstituted alkyl group and * indicates where the moiety is connected to the remainder of the nucleotide or nucleoside). In some aspects, the linkers connect the bases of nucleotides to labels such as, for example, the dye compounds described herein.

In particular embodiments, the length of the linker between a fluorescent dye (fluorophore) and a guanine base can be altered, for example, by introducing a polyethylene glycol spacer group, thereby increasing the fluorescence intensity compared to the same fluorophore attached to the guanine base through other linkages known in the art. Exemplary linkers and their properties are set forth in PCT Publication No. WO2007020457 (herein incorporated by reference). The design of linkers, and especially their increased length, can allow improvements in the brightness of fluorophores attached to the guanine bases of guanosine nucleotides when incorporated into polynucleotides such as DNA. Thus, when the dye is for use in any method of analysis which requires detection of a fluorescent dye label attached to a guanine-containing nucleotide, it is advantageous if the linker comprises a spacer group of formula —$((CH_2)_2O)_n$—, wherein n is an integer between 2 and 50, as described in WO 2007/020457.

Nucleosides and nucleotides may be labeled at sites on the sugar or nucleobase. As known in the art, a "nucleotide" consists of a nitrogenous base, a sugar, and one or more phosphate groups. In RNA, the sugar is ribose and in DNA is a deoxyribose, i.e., a sugar lacking a hydroxyl group that is present in ribose. The nitrogenous base is a derivative of purine or pyrimidine. The purines are adenine (A) and guanine (G), and the pyrimidines are cytosine (C) and thymine (T) or in the context of RNA, uracil (U). The C-1 atom of deoxyribose is bonded to N-1 of a pyrimidine or N-9 of a purine. A nucleotide is also a phosphate ester of a nucleoside, with esterification occurring on the hydroxyl group attached to the C-3 or C-5 of the sugar. Nucleotides are usually mono, di- or triphosphates.

A "nucleoside" is structurally similar to a nucleotide but is missing the phosphate moieties. An example of a nucleoside analog would be one in which the label is linked to the base and there is no phosphate group attached to the sugar molecule.

Although the base is usually referred to as a purine or pyrimidine, the skilled person will appreciate that derivatives and analogues are available which do not alter the capability of the nucleotide or nucleoside to undergo Watson-Crick base pairing. "Derivative" or "analogue" means a compound or molecule whose core structure is the same as, or closely resembles that of a parent compound but which has a chemical or physical modification, such as, for example, a different or additional side group, which allows the derivative nucleotide or nucleoside to be linked to another molecule. For example, the base may be a deazapurine. In particular embodiments, the derivatives should be capable of undergoing Watson-Crick pairing. "Derivative" and "analogue" also include, for example, a synthetic nucleotide or nucleoside derivative having modified base moieties and/or modified sugar moieties. Such derivatives and analogues are discussed in, for example, Scheit, *Nucleotide analogs* (John Wiley & Son, 1980) and Uhlman et al., *Chemical Reviews* 90:543-584, 1990. Nucleotide analogues can also comprise modified phosphodiester linkages including phosphorothioate, phosphorodithioate, alkyl-phosphonate, phosphoranilidate, phosphoramidate linkages and the like.

A dye may be attached to any position on the nucleotide base, for example, through a linker. In particular embodiments, Watson-Crick base pairing can still be carried out for the resulting analog. Particular nucleobase labeling sites include the C5 position of a pyrimidine base or the C7 position of a 7-deaza purine base. As described above a linker group may be used to covalently attach a dye to the nucleoside or nucleotide.

In particular embodiments the labeled nucleoside or nucleotide may be enzymatically incorporable and enzymatically extendable. Accordingly, a linker moiety may be of sufficient length to connect the nucleotide to the compound such that the compound does not significantly interfere with the overall binding and recognition of the nucleotide by a nucleic acid replication enzyme. Thus, the linker can also comprise a spacer unit. The spacer distances, for example, the nucleotide base from a cleavage site or label.

Nucleosides or nucleotides labeled with the dyes described herein may have the formula:

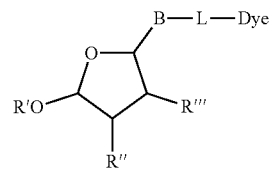

where
Dye is a dye compound,
B is a nucleobase, such as, for example uracil, thymine, cytosine, adenine, guanine and the like,
L is an optional linker group which may or may not be present,
R' can be H, monophosphate, diphosphate, triphosphate, thiophosphate, a phosphate ester analog, —O— attached to a reactive phosphorous containing group, or —O— protected by a blocking group,
R" can be H, OH, a phosphoramidite, or a 3'-OH blocking group, and
R''' is H or OH.

Where R" is phosphoramidite, R' is an acid-cleavable hydroxyl protecting group which allows subsequent monomer coupling under automated synthesis conditions.

In a particular embodiment, the blocking group is separate and independent of the dye compound, i.e., not attached to it. Alternatively, the dye may comprise all or part of the 3'-OH blocking group. Thus R" can be a 3'-OH blocking group which may or may not comprise the dye compound.

In yet another alternative embodiment, there is no blocking group on the 3' carbon of the pentose sugar and the dye (or dye and linker construct) attached to the base, for example, can be of a size or structure sufficient to act as a block to the incorporation of a further nucleotide. Thus, the block can be due to steric hindrance or can be due to a combination of size, charge and structure, whether or not the dye is attached to the 3' position of the sugar.

In still yet another alternative embodiment, the blocking group is present on the 2' or 4' carbon of the pentose sugar and can be of a size or structure sufficient to act as a block to the incorporation of a further nucleotide.

The use of a blocking group allows polymerization to be controlled, such as by stopping extension when a modified nucleotide is incorporated. If the blocking effect is reversible, for example, by way of non-limiting example by changing chemical conditions or by removal of a chemical block, extension can be stopped at certain points and then allowed to continue.

In another particular embodiment, a 3'-OH blocking group will comprise a moiety disclosed in WO2004/018497 and WO2014/139596, which are hereby incorporated by references. For example the blocking group may be azidomethyl (—CH$_2$N$_3$) or substituted azidomethyl (e.g., —CH(CHF$_2$)N$_3$ or CH(CH$_2$F)N$_3$), or allyl.

In a particular embodiment, the linker (between dye and nucleotide) and blocking group are both present and are separate moieties. In particular embodiments, the linker and blocking group are both cleavable under substantially similar conditions. Thus, deprotection and deblocking processes may be more efficient because only a single treatment will be required to remove both the dye compound and the blocking group. However, in some embodiments a linker and blocking group need not be cleavable under similar conditions, instead being individually cleavable under distinct conditions.

The disclosure also encompasses polynucleotides incorporating dye compounds. Such polynucleotides may be DNA or RNA comprised respectively of deoxyribonucleotides or ribonucleotides joined in phosphodiester linkage. Polynucleotides may comprise naturally occurring nucleotides, non-naturally occurring (or modified) nucleotides other than the labeled nucleotides described herein or any combination thereof, in combination with at least one modified nucleotide (e.g., labeled with a dye compound) as set forth herein. Polynucleotides according to the disclosure may also include non-natural backbone linkages and/or non-nucleotide chemical modifications. Chimeric structures comprised of mixtures of ribonucleotides and deoxyribonucleotides comprising at least one labeled nucleotide are also contemplated.

Non-limiting exemplary labeled nucleotides as described herein include:

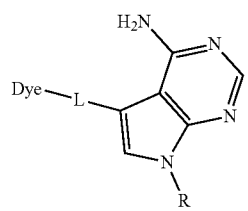

A

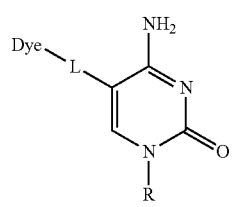

C

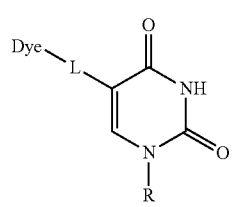

T

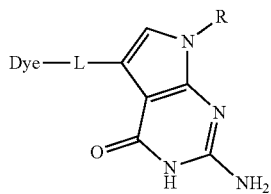

G

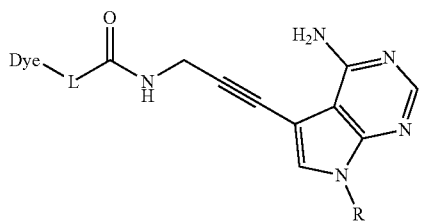

A

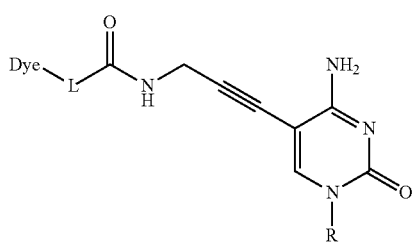

C

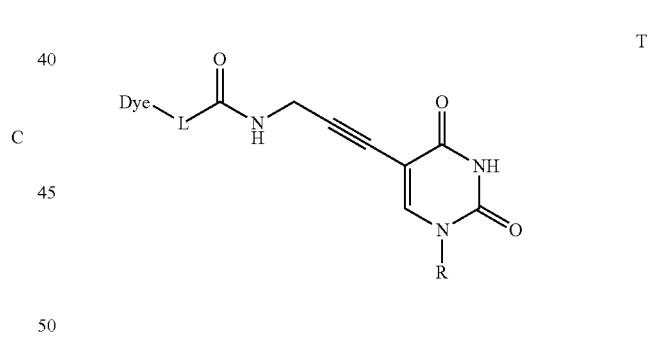

T

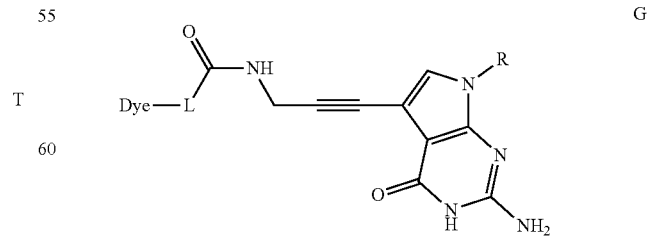

G wherein L represents a linker and R represents a sugar residue as described above.

In some embodiments, non-limiting exemplary fluorescent dye conjugates are shown below:

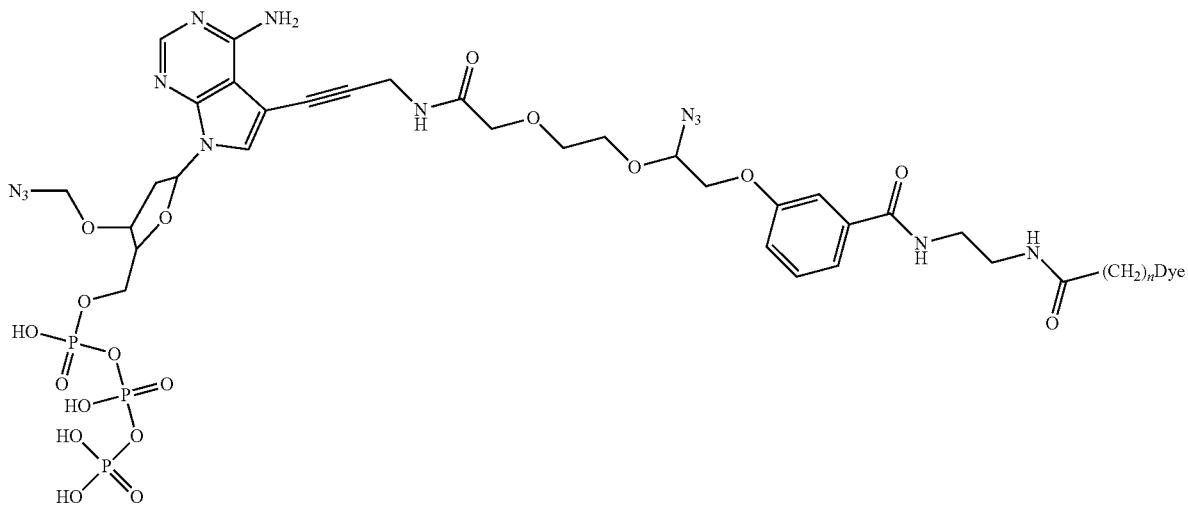

ffA-LN3-Dye

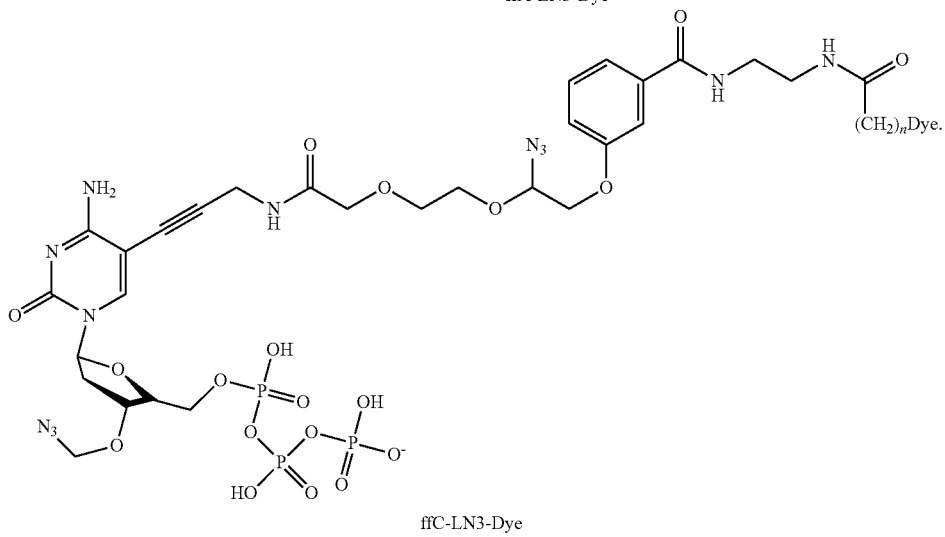

ffC-LN3-Dye

Kits

The present disclosure also provides kits including modified nucleosides and/or nucleotides labeled with dyes. Such kits will generally include at least one modified nucleotide or nucleoside labeled with a dye set forth herein together with at least one further component. The further component(s) may be one or more of the components identified in a method set forth herein or in the Examples section below. Some non-limiting examples of components that can be combined into a kit of the present disclosure are set forth below.

In a particular embodiment, a kit can include at least one modified nucleotide or nucleoside labeled with a dye set forth herein together with modified or unmodified nucleotides or nucleosides. For example, modified nucleotides labeled with dyes according to the disclosure may be supplied in combination with unlabeled or native nucleotides, and/or with fluorescently labeled nucleotides or any combination thereof. Accordingly, the kits may comprise modified nucleotides labeled with dyes according to the disclosure and modified nucleotides labeled with other, for example, prior art dye compounds. Combinations of nucleotides may be provided as separate individual components (e.g., one nucleotide type per vessel or tube) or as nucleotide mixtures (e.g., two or more nucleotides mixed in the same vessel or tube).

Where kits comprise a plurality, particularly two, or three, or more particularly four, modified nucleotides labeled with a dye compound, the different nucleotides may be labeled with different dye compounds, or one may be dark, with no dye compounds. Where the different nucleotides are labeled with different dye compounds, it is a feature of the kits that the dye compounds are spectrally distinguishable fluorescent dyes. As used herein, the term "spectrally distinguishable fluorescent dyes" refers to fluorescent dyes that emit fluorescent energy at wavelengths that can be distinguished by fluorescent detection equipment (for example, a commercial capillary-based DNA sequencing platform) when two or more such dyes are present in one sample. When two modified nucleotides labeled with fluorescent dye compounds are supplied in kit form, it is a feature of some embodiments that the spectrally distinguishable fluorescent dyes can be excited at the same wavelength, such as, for example by the same laser. When four modified nucleotides labeled with fluorescent dye compounds are supplied in kit form, it is a feature of some embodiments that two of the spectrally distinguishable fluorescent dyes can both be excited at one wavelength and the other two spectrally distinguishable dyes can both be excited at another wavelength. Particular excitation wavelengths are 488 nm and 532 nm.

In one embodiment, a kit includes a modified nucleotide labeled with a compound of the present disclosure and a second modified nucleotide labeled with a second dye wherein the dyes have a difference in absorbance maximum of at least 10 nm, particularly 20 nm to 50 nm. More particularly, the two dye compounds have Stokes shifts of between 15-40 nm where "Stokes shift" is the distance between the peak absorption and peak emission wavelengths.

In a further embodiment, a kit can further include two other modified nucleotides labeled with fluorescent dyes wherein the dyes are excited by the same laser at 532 nm. The dyes can have a difference in absorbance maximum of at least 10 nm, particularly 20 nm to 50 nm. More particularly the two dye compounds can have Stokes shifts of between 20-40 nm. Particular dyes which are spectrally distinguishable from dyes of the present disclosure and which meet the above criteria are polymethine analogues as described in U.S. Pat. No. 5,268,486 (for example Cy3) or WO 0226891 (Alexa 532; Molecular Probes A20106) or unsymmetrical polymethines as disclosed in U.S. Pat. No. 6,924,372, each of which is incorporated herein by reference. Alternative dyes include rhodamine analogues, for example tetramethyl rhodamine and analogues thereof.

In an alternative embodiment, the kits of the disclosure may contain nucleotides where the same base is labeled with two different compounds. A first nucleotide may be labeled with a compound of the disclosure. A second nucleotide may be labeled with a spectrally distinct compound, for example a 'green' dye absorbing at less than 600 nm. A third nucleotide may be labeled as a mixture of the compound of the disclosure and the spectrally distinct compound, and the fourth nucleotide may be 'dark' and contain no label. In simple terms, therefore, the nucleotides 1-4 may be labeled 'blue', 'green', 'blue/green', and dark. To simplify the instrumentation further, four nucleotides can be labeled with two dyes excited with a single laser, and thus the labeling of nucleotides 1-4 may be 'blue 1', 'blue 2', 'blue 1/blue 2', and dark.

Nucleotides may contain two dyes of the present disclosure. A kit may contain two or more nucleotides labeled with dyes of the disclosure. Kits may contain a further nucleotide where the nucleotide is labeled with a dye that absorbs in the region of 520 nm to 560 nm. Kits may further contain an unlabeled nucleotide.

Although kits are exemplified herein in regard to configurations having different nucleotides that are labeled with different dye compounds, it will be understood that kits can include 2, 3, 4 or more different nucleotides that have the same dye compound.

In particular embodiments, a kit may include a polymerase enzyme capable of catalyzing incorporation of the modified nucleotides into a polynucleotide. Other components to be included in such kits may include buffers and the like. The modified nucleotides labeled with dyes according to the disclosure, and other any nucleotide components including mixtures of different nucleotides, may be provided in the kit in a concentrated form to be diluted prior to use.

In such embodiments a suitable dilution buffer may also be included. Again, one or more of the components identified in a method set forth herein can be included in a kit of the present disclosure.

Methods of Sequencing

Modified nucleotides (or nucleosides) comprising a dye compound according to the present disclosure may be used in any method of analysis such as method that include detection of a fluorescent label attached to a nucleotide or nucleoside, whether on its own or incorporated into or associated with a larger molecular structure or conjugate. In this context the term "incorporated into a polynucleotide" can mean that the 5' phosphate is joined in phosphodiester linkage to the 3' hydroxyl group of a second (modified or unmodified) nucleotide, which may itself form part of a longer polynucleotide chain. The 3' end of a modified nucleotide set forth herein may or may not be joined in phosphodiester linkage to the 5' phosphate of a further (modified or unmodified) nucleotide. Thus, in one non-limiting embodiment, the disclosure provides a method of detecting a modified nucleotide incorporated into a polynucleotide which comprises: (a) incorporating at least one modified nucleotide of the disclosure into a polynucleotide and (b) detecting the modified nucleotide(s) incorporated into the polynucleotide by detecting the fluorescent signal from the dye compound attached to said modified nucleotide(s).

This method can include: a synthetic step (a) in which one or more modified nucleotides according to the disclosure are incorporated into a polynucleotide and a detection step (b) in which one or more modified nucleotide(s) incorporated into the polynucleotide are detected by detecting or quantitatively measuring their fluorescence.

Some embodiments of the present application are directed to methods of sequencing including: (a) incorporating at least one labeled nucleotide as described herein into a polynucleotide; and (b) detecting the labeled nucleotide(s) incorporated into the polynucleotide by detecting the fluorescent signal from the new fluorescent dye attached to said modified nucleotide(s).

In one embodiment, at least one modified nucleotide is incorporated into a polynucleotide in the synthetic step by the action of a polymerase enzyme. However, other methods of joining modified nucleotides to polynucleotides, such as, for example, chemical oligonucleotide synthesis or ligation of labeled oligonucleotides to unlabeled oligonucleotides, can be used. Therefore, the term "incorporating," when used in reference to a nucleotide and polynucleotide, can encompass polynucleotide synthesis by chemical methods as well as enzymatic methods.

In a specific embodiment, a synthetic step is carried out and may optionally comprise incubating a template polynucleotide strand with a reaction mixture comprising fluorescently labeled modified nucleotides of the disclosure. A polymerase can also be provided under conditions which permit formation of a phosphodiester linkage between a free 3' hydroxyl group on a polynucleotide strand annealed to the template polynucleotide strand and a 5' phosphate group on the modified nucleotide. Thus, a synthetic step can include formation of a polynucleotide strand as directed by complementary base-pairing of nucleotides to a template strand.

In all embodiments of the methods, the detection step may be carried out while the polynucleotide strand into which the labeled nucleotides are incorporated is annealed to a template strand, or after a denaturation step in which the two strands are separated. Further steps, for example chemical or enzymatic reaction steps or purification steps, may be included between the synthetic step and the detection step. In particular, the target strand incorporating the labeled nucleotide(s) may be isolated or purified and then processed further or used in a subsequent analysis. By way of example, target polynucleotides labeled with modified nucleotide(s) as described herein in a synthetic step may be subsequently used as labeled probes or primers. In other embodiments, the product of the synthetic step set forth herein may be subject to further reaction steps and, if desired, the product of these subsequent steps purified or isolated.

Suitable conditions for the synthetic step will be well known to those familiar with standard molecular biology techniques. In one embodiment, a synthetic step may be analogous to a standard primer extension reaction using nucleotide precursors, including modified nucleotides as described herein, to form an extended target strand complementary to the template strand in the presence of a suitable polymerase enzyme. In other embodiments, the synthetic step may itself form part of an amplification reaction producing a labeled double stranded amplification product comprised of annealed complementary strands derived from copying of the target and template polynucleotide strands. Other exemplary synthetic steps include nick translation, strand displacement polymerization, random primed DNA labeling, etc. A particularly useful polymerase enzyme for a synthetic step is one that is capable of catalyzing the incorporation of modified nucleotides as set forth herein. A variety of naturally occurring or modified polymerases can be used. By way of example, a thermostable polymerase can be used for a synthetic reaction that is carried out using thermocycling conditions, whereas a thermostable polymerase may not be desired for isothermal primer extension reactions. Suitable thermostable polymerases which are capable of incorporating the modified nucleotides according to the disclosure include those described in WO 2005/024010 or WO06120433, each of which is incorporated herein by reference. In synthetic reactions which are carried out at lower temperatures such as 37° C., polymerase enzymes need not necessarily be thermostable polymerases, therefore the choice of polymerase will depend on a number of factors such as reaction temperature, pH, strand-displacing activity and the like.

In specific non-limiting embodiments, the disclosure encompasses methods of nucleic acid sequencing, re-sequencing, whole genome sequencing, single nucleotide polymorphism scoring, any other application involving the detection of the modified nucleotide or nucleoside labeled with dyes set forth herein when incorporated into a polynucleotide. Any of a variety of other applications benefitting the use of polynucleotides labeled with the modified nucleotides comprising fluorescent dyes can use modified nucleotides or nucleosides with dyes set forth herein.

In a particular embodiment the disclosure provides use of modified nucleotides comprising dye compounds according to the disclosure in a polynucleotide sequencing-by-synthesis reaction. Sequencing-by-synthesis generally involves sequential addition of one or more nucleotides or oligonucleotides to a growing polynucleotide chain in the 5' to 3' direction using a polymerase or ligase in order to form an extended polynucleotide chain complementary to the template nucleic acid to be sequenced. The identity of the base present in one or more of the added nucleotide(s) can be determined in a detection or "imaging" step. The identity of the added base may be determined after each nucleotide incorporation step. The sequence of the template may then be inferred using conventional Watson-Crick base-pairing rules. The use of the modified nucleotides labeled with dyes set forth herein for determination of the identity of a single base may be useful, for example, in the scoring of single nucleotide polymorphisms, and such single base extension reactions are within the scope of this disclosure.

In an embodiment of the present disclosure, the sequence of a template polynucleotide is determined by detecting the incorporation of one or more nucleotides into a nascent strand complementary to the template polynucleotide to be sequenced through the detection of fluorescent label(s) attached to the incorporated nucleotide(s). Sequencing of the template polynucleotide can be primed with a suitable primer (or prepared as a hairpin construct which will contain the primer as part of the hairpin), and the nascent chain is extended in a stepwise manner by addition of nucleotides to the 3' end of the primer in a polymerase-catalyzed reaction.

In particular embodiments, each of the different nucleotide triphosphates (A, T, G and C) may be labeled with a unique fluorophore and also comprises a blocking group at the 3' position to prevent uncontrolled polymerization. Alternatively, one of the four nucleotides may be unlabeled (dark). The polymerase enzyme incorporates a nucleotide into the nascent chain complementary to the template polynucleotide, and the blocking group prevents further incorporation of nucleotides. Any unincorporated nucleotides can be washed away and the fluorescent signal from each incorporated nucleotide can be "read" optically by suitable means, such as a charge-coupled device using laser excitation and suitable emission filters. The 3'-blocking group and fluorescent dye compounds can then be removed (deprotected) (simultaneously or sequentially) to expose the nascent chain for further nucleotide incorporation. Typically, the identity of the incorporated nucleotide will be determined after each incorporation step, but this is not strictly essential. Similarly, U.S. Pat. No. 5,302,509 (which is incorporated herein by reference) discloses a method to sequence polynucleotides immobilized on a solid support.

The method, as exemplified above, utilizes the incorporation of fluorescently labeled, 3'-blocked nucleotides A, G, C, and T into a growing strand complementary to the immobilized polynucleotide, in the presence of DNA polymerase. The polymerase incorporates a base complementary to the target polynucleotide but is prevented from further addition by the 3'-blocking group. The label of the incorporated nucleotide can then be determined, and the blocking group removed by chemical cleavage to allow further polymerization to occur. The nucleic acid template to be sequenced in a sequencing-by-synthesis reaction may be any polynucleotide that it is desired to sequence. The nucleic acid template for a sequencing reaction will typically comprise a double stranded region having a free 3' hydroxyl group that serves as a primer or initiation point for the addition of further nucleotides in the sequencing reaction. The region of the template to be sequenced will overhang this free 3' hydroxyl group on the complementary strand. The overhanging region of the template to be sequenced may be single stranded but can be double-stranded, provided that a "nick is present" on the strand complementary to the template strand to be sequenced to provide a free 3' OH group for initiation of the sequencing reaction. In such embodiments, sequencing may proceed by strand displacement. In certain embodiments, a primer bearing the free 3' hydroxyl group may be added as a separate component (e.g., a short oligonucleotide) that hybridizes to a single-stranded region of the template to be sequenced. Alternatively, the primer and the template strand to be sequenced may each form part of a partially self-complementary nucleic acid strand capable of forming an intra-molecular duplex, such as for example a hairpin loop structure. Hairpin polynucleotides and methods by which they may be attached to solid supports are disclosed in PCT Publication Nos. WO0157248 and WO2005/047301, each of which is incorporated herein by reference. Nucleotides can be added successively to a growing primer, resulting in synthesis of a polynucleotide chain in the 5' to 3' direction. The nature of the base which has been added may be determined, particularly but not necessarily after each nucleotide addition, thus providing sequence information for the nucleic acid template. Thus, a nucleotide is incorporated into a nucleic acid strand (or polynucleotide) by joining of the nucleotide to the free 3' hydroxyl group of the nucleic acid strand via formation of a phosphodiester linkage with the 5' phosphate group of the nucleotide.

The nucleic acid template to be sequenced may be DNA or RNA, or even a hybrid molecule comprised of deoxynucleotides and ribonucleotides. The nucleic acid template may comprise naturally occurring and/or non-naturally occurring nucleotides and natural or non-natural backbone linkages, provided that these do not prevent copying of the template in the sequencing reaction.

In certain embodiments, the nucleic acid template to be sequenced may be attached to a solid support via any suitable linkage method known in the art, for example via covalent attachment. In certain embodiments template polynucleotides may be attached directly to a solid support (e.g., a silica-based support). However, in other embodiments of the disclosure the surface of the solid support may be modified in some way so as to allow either direct covalent attachment of template polynucleotides, or to immobilize the template polynucleotides through a hydrogel or polyelectrolyte multilayer, which may itself be non-covalently attached to the solid support.

Arrays in which polynucleotides have been directly attached to silica-based supports are those for example disclosed in WO00006770 (incorporated herein by reference), wherein polynucleotides are immobilized on a glass support by reaction between a pendant epoxide group on the glass with an internal amino group on the polynucleotide. In addition, polynucleotides can be attached to a solid support by reaction of a sulfur-based nucleophile with the solid support, for example, as described in WO2005/047301 (incorporated herein by reference). A still further example of solid-supported template polynucleotides is where the template polynucleotides are attached to hydrogel supported upon silica-based or other solid supports, for example, as described in WO00/31148, WO01/01143, WO02/12566, WO03/014392, U.S. Pat. No. 6,465,178 and WO00/53812, each of which is incorporated herein by reference.

A particular surface to which template polynucleotides may be immobilized is a polyacrylamide hydrogel. Polyacrylamide hydrogels are described in the references cited above and in WO2005/065814, which is incorporated herein by reference. Specific hydrogels that may be used include those described in WO 2005/065814 and U.S. Pub. No. 2014/0079923. In one embodiment, the hydrogel is PAZAM (poly(N-(5-azidoacetamidylpentyl) acrylamide-co-acrylamide)).

DNA template molecules can be attached to beads or microparticles, for example, as described in U.S. Pat. No. 6,172,218 (which is incorporated herein by reference). Attachment to beads or microparticles can be useful for sequencing applications. Bead libraries can be prepared where each bead contains different DNA sequences. Exemplary libraries and methods for their creation are described in Nature, 437, 376-380 (2005); Science, 309, 5741, 1728-1732 (2005), each of which is incorporated herein by reference. Sequencing of arrays of such beads using nucleotides set forth herein is within the scope of the disclosure.

Template(s) that are to be sequenced may form part of an "array" on a solid support, in which case the array may take any convenient form. Thus, the method of the disclosure is applicable to all types of high-density arrays, including single-molecule arrays, clustered arrays, and bead arrays. Modified nucleotides labeled with dye compounds of the present disclosure may be used for sequencing templates on essentially any type of array, including but not limited to those formed by immobilization of nucleic acid molecules on a solid support.

However, the modified nucleotides labeled with dye compounds of the disclosure are particularly advantageous in the context of sequencing of clustered arrays. In clustered arrays, distinct regions on the array (often referred to as sites, or features) comprise multiple polynucleotide template molecules. Generally, the multiple polynucleotide molecules are not individually resolvable by optical means and are instead detected as an ensemble. Depending on how the array is formed, each site on the array may comprise multiple copies of one individual polynucleotide molecule (e.g., the site is homogenous for a particular single- or double-stranded nucleic acid species) or even multiple copies of a small number of different polynucleotide molecules (e.g., multiple copies of two different nucleic acid species). Clustered arrays of nucleic acid molecules may be produced using techniques generally known in the art. By way of example, WO 98/44151 and WO00/18957, each of which is incorporated herein, describe methods of amplification of nucleic acids wherein both the template and amplification products remain immobilized on a solid support in order to form arrays comprised of clusters or "colonies" of immobilized nucleic acid molecules. The nucleic acid molecules present on the clustered arrays prepared according to these methods are suitable templates for sequencing using the modified nucleotides labeled with dye compounds of the disclosure.

The modified nucleotides labeled with dye compounds of the present disclosure are also useful in sequencing of templates on single molecule arrays. The term "single molecule array" or "SMA" as used herein refers to a population of polynucleotide molecules, distributed (or arrayed) over a solid support, wherein the spacing of any individual polynucleotide from all others of the population is such that it is possible to individually resolve the individual polynucleotide molecules. The target nucleic acid molecules immobilized onto the surface of the solid support can thus be capable of being resolved by optical means in some embodiments. This means that one or more distinct signals, each representing one polynucleotide, will occur within the resolvable area of the particular imaging device used.

Single molecule detection may be achieved wherein the spacing between adjacent polynucleotide molecules on an array is at least 100 nm, more particularly at least 250 nm, still more particularly at least 300 nm, even more particularly at least 350 nm. Thus, each molecule is individually resolvable and detectable as a single molecule fluorescent point, and fluorescence from said single molecule fluorescent point also exhibits single step photobleaching.

The terms "individually resolved" and "individual resolution" are used herein to specify that, when visualized, it is possible to distinguish one molecule on the array from its neighboring molecules. Separation between individual molecules on the array will be determined, in part, by the particular technique used to resolve the individual molecules. The general features of single molecule arrays will be understood by reference to published applications WO00/06770 and WO 01/57248, each of which is incorporated herein by reference. Although one use of the modified nucleotides of the disclosure is in sequencing-by-synthesis reactions, the utility of the modified nucleotides is not limited to such methods. In fact, the nucleotides may be used advantageously in any sequencing methodology which requires detection of fluorescent labels attached to nucleotides incorporated into a polynucleotide.

In particular, the modified nucleotides labeled with dye compounds of the disclosure may be used in automated fluorescent sequencing protocols, particularly fluorescent dye-terminator cycle sequencing based on the chain termination sequencing method of Sanger and co-workers. Such methods generally use enzymes and cycle sequencing to incorporate fluorescently labeled dideoxynucleotides in a primer extension sequencing reaction. So-called Sanger sequencing methods, and related protocols (Sanger-type), utilize randomized chain termination with labeled dideoxynucleotides.

Thus, the present disclosure also encompasses modified nucleotides labeled with dye compounds which are dideoxynucleotides lacking hydroxyl groups at both of the 3' and 2' positions, such modified dideoxynucleotides being suitable for use in Sanger type sequencing methods and the like.

Modified nucleotides labeled with dye compounds of the present disclosure incorporating 3' blocking groups, it will be recognized, may also be of utility in Sanger methods and related protocols since the same effect achieved by using modified dideoxy nucleotides may be achieved by using modified nucleotides having 3'-OH blocking groups: both prevent incorporation of subsequent nucleotides. Where nucleotides according to the present disclosure, and having a 3' blocking group are to be used in Sanger-type sequencing methods it will be appreciated that the dye compounds or detectable labels attached to the nucleotides need not be connected via cleavable linkers, since in each instance where a labeled nucleotide of the disclosure is incorporated; no nucleotides need to be subsequently incorporated and thus the label need not be removed from the nucleotide.

EXAMPLES

Additional embodiments are disclosed in further detail in the following examples, which are not in any way intended to limit the scope of the claims.

Additional embodiments are disclosed in further detail in the following examples, which are not in any way intended to limit the scope of the claims. Table 2 summarizes spectral properties of the new coumarin fluorescent dyes disclosed in the examples. Table 3 summarizes the structure and spectral properties of various nucleotides labeled with new dyes disclosed herein.

Example 1-1-1: 7-(5-Carboxypentyl)amino-3-(benzothiazol-2-yl)coumarin

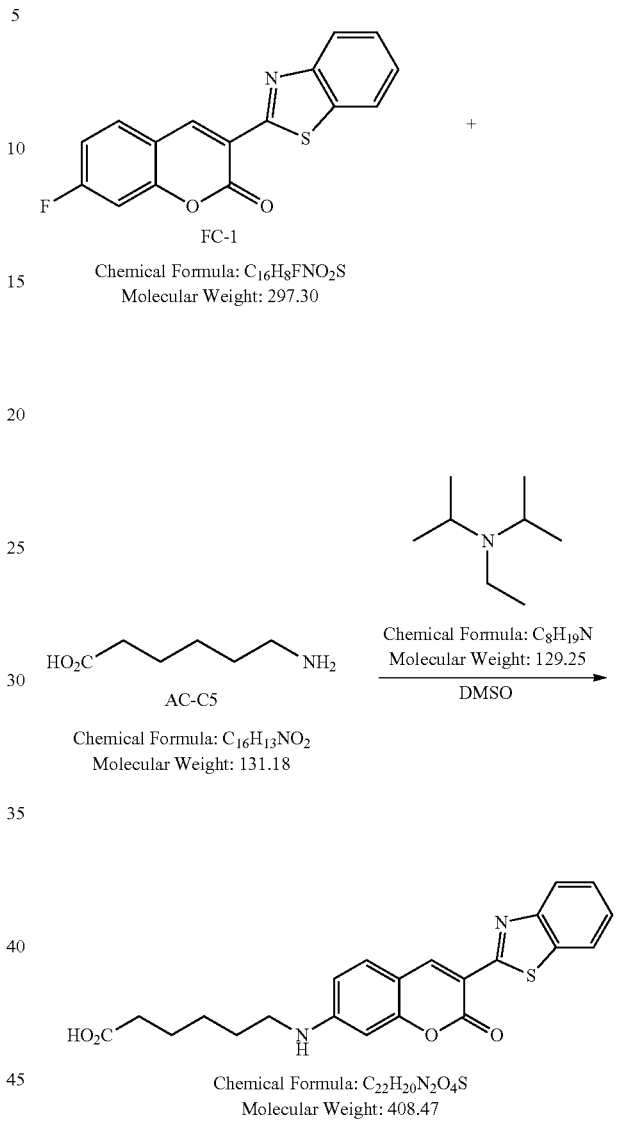

3-(Benzothiazol-2-yl)-7-fluoro-coumarin derivative (FC-1, 0.4 g, 1.345 mmol, 1 eqv) and 6-aminohexanoic acid (AC-05, 0.25 g, 1.906 mmol, 1.417 eqv) was added to anhydrous dimethyl sulfoxide (DMSO, 3 mL). After the addition was complete, the mixture was stirred for a few minutes at room temperature and then N,N-diisopropyl-N-ethylamine (DIPEA, 0.25 g, 2 mmol, 2 eqv) was added to this mixture. The reaction mixture was stirred for 3 hours at 120° C. After standing at room temperature for 1 hour, the yellow, semi-solid reaction mixture was diluted with water (5 mL) and stirred overnight. The resulting precipitate was collected by suction filtration. Yield 0.36 g (65.5%). MS (DUIS): MW Calculated 408.47. Found m/z: (+) 409 (M+1)$^+$; (−), 407 (M−1)$^-$. $^1$H NMR (400 MHz, DMSO-d$_6$) δ: 12.03 (m, 2H), 9.00 (s, 1H), 8.12 (d, J=7.9 Hz, 1H), 7.99 (d, J=8.1 Hz, 1H), 6.73 (dd, J=8.8, 2.1 Hz, 1H), 6.54 (d, J=2.0 Hz, 1H), 3.18 (q, J=6.5 Hz, 2H), 2.23 (t, J=7.3 Hz, 2H), 1.57 (dp, J=14.7, 7.2 Hz, 4H), 1.39 (dq, J=9.2, 4.5, 3.5 Hz, 2H).

Example 1-1-2: 7-(5-Carboxypentyl)amino-3-(benzimidazol-2-yl)coumarin

Example 1-1-3: 7-(2-Carboxyethyl)amino-3-(benzothiazol-2-yl)coumarin

Step A: 7-[2-(t-Butyloxycarbonyl)ethyl]amino-3-(benzothiazol-2-yl)coumarin

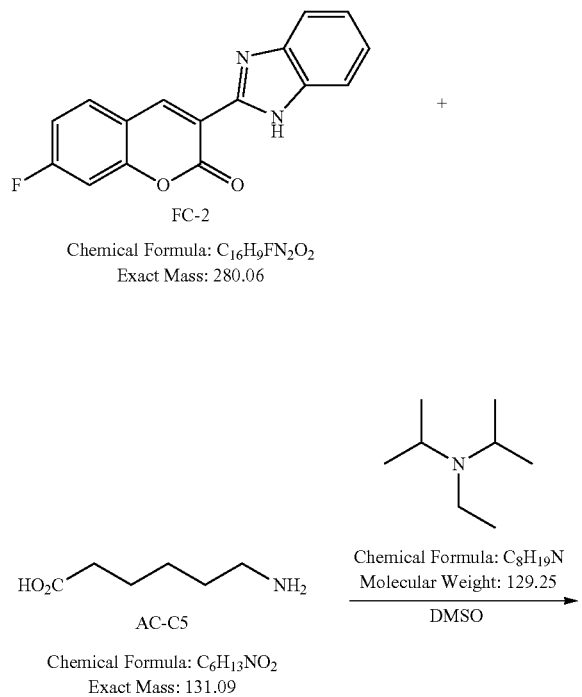

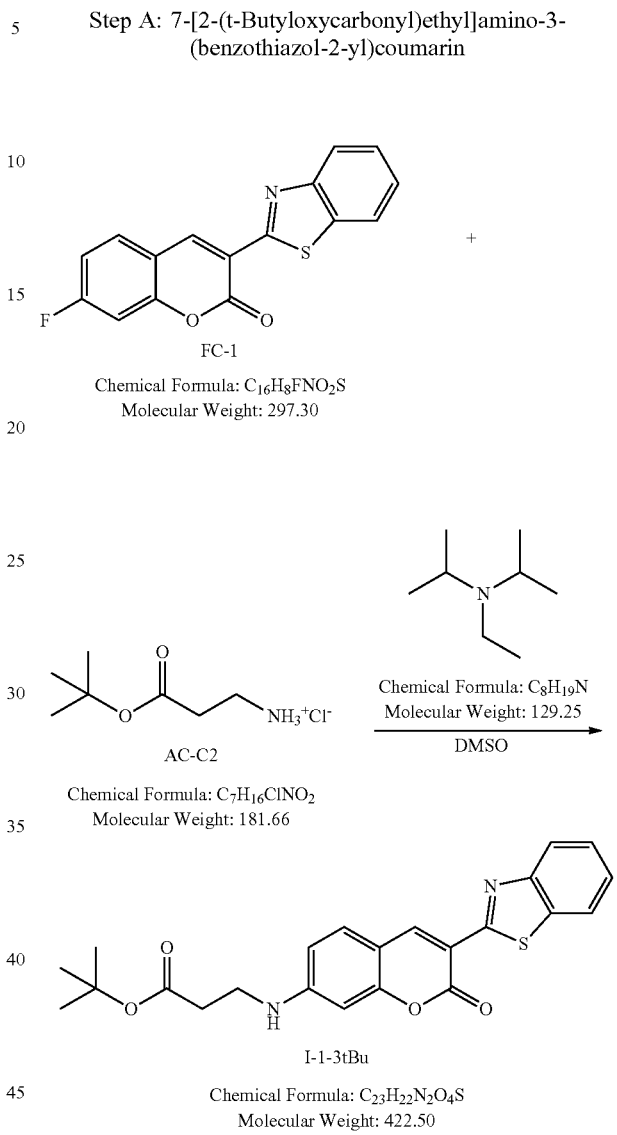

3-(Benzimidazol-2-yl)-7-fluoro-coumarin (FC-2, 0.28 g, 1 mmol, 1 eqv) and 6-aminohexanoic acid (AC-05, 0.13 g, 1 mmol, 1 eqv) was added to anhydrous dimethyl sulfoxide (DMSO, 2 mL). The resulting mixture was stirred for a few minutes at room temperature and then DIPEA (0.25 g, 2 mmol, 2 eqv) was added. The reaction mixture was stirred for 4 hours at temperature 130° C. Additional portions of 6-aminohexanoic acid (AC-1, 0.13 g, 1 mmol, 1 eqv) and DIPEA (0.26 g, 2 mmol, 2 eqv) was added to the reaction mixture and heating was continued at 130° C. was continued for 5 hours. After standing at room temperature for 1 hour, the pale-yellow reaction mixture was diluted with water (5 mL) and stirred overnight. The resulting precipitate was collected by suction filtration. Yield 0.26 g (68.5%). Purity, structure and composition of the product were confirmed by HPLC, NMR and LCMS. MS (DUIS): MW Calculated 391.15. Found m/z: (+) 392 (M+1)$^+$; (−) 390 (M−1)$^-$, 781 (2M−1)$^-$.

3-(Benzothiazol-2-yl)-7-fluoro-coumarin (FC-1, 0.3 g, 1.01 mmol, 1 eqv) and t-butyl 3-aminopropionate hydrochloride (AC-C2, 0.2 g, 1.1 mmol, 1.09 eqv) was added to anhydrous dimethyl sulfoxide (DMSO, 2 mL) and the resulting mixture was stirred for a few minutes at room temperature and then DIPEA (0.26 g, 2 mmol, 2 eqv) was added. The resulting mixture was stirred for 2 hours at 100° C. After standing at room temperature for 1 hour, the yellow reaction mixture was diluted with water (7 mL) and was stirred overnight. The resulting precipitate was collected by suction filtration. Yield 0.38 g (69%). MS (DUIS): MW Calculated 422.13. Found m/z: (+) 423 (M+1)$^+$; (−), 421 (M−1)$^-$. $^1$H NMR (400 MHz, DMSO-d$_6$) δ: 9.28 (s, 1H), 9.01 (s, 1H), 8.27-8.16 (m, 1H), 8.10 (tt, J=8.3, 0.9 Hz, 2H), 8.05-7.92 (m, 1H), 7.72 (d, J=8.8 Hz, 1H), 7.66-7.55 (m, 1H), 7.51 (dddd, J=11.4, 8.2, 7.1, 1.3 Hz, 2H), 7.46-7.32 (m, 2H), 6.74 (dd, J=8.7, 2.1 Hz, 1H), 6.58 (d, J=2.1 Hz, 1H), 3.41 (q, J=6.3 Hz, 2H), 2.55 (t, J=6.4 Hz, 2H), 1.41 (s, 9H).

Step B

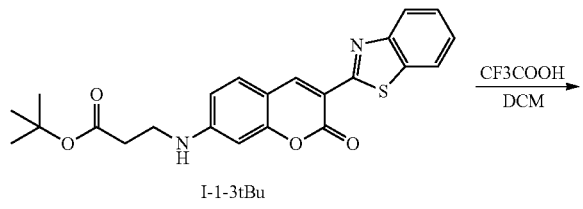

I-1-3tBu

Chemical Formula: C₂₃H₂₂N₂O₄S
Molecular Weight: 422.50

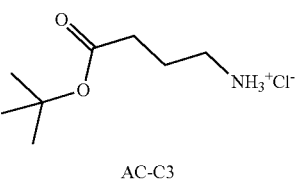

AC-C3

Chemical Formula: C₈H₁₈ClNO₂
Molecular Weight: 195.69

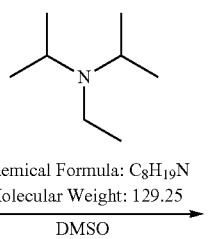

Chemical Formula: C₈H₁₉N
Molecular Weight: 129.25

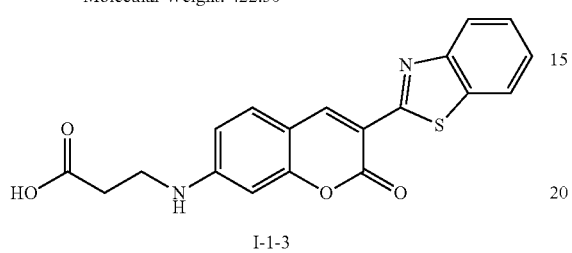

I-1-3

Chemical Formula: C₁₉H₁₄N₂O₄S
Molecular Weight: 366.39

A solution of 7-[2-(t-butyloxycarbonyl)ethyl]amino-3-(benzothiazol-2-yl)coumarin (I-1-3tBu, 0.2 g, 0.473 mmol) in anhydrous dichloromethane (20 mL) was treated with trifluoroacetic acid (0.5 mL) and the resulting mixture was stirred for 24 hours at room temperature. The solvents were distilled off and the residue was triturated with water (10 mL). The resulting precipitate was collected by suction filtration. Yield 0.15 g (86%). Purity, structure and composition were confirmed by HPLC, NMR and LCMS. MS (DUIS): MW Calculated 366.39. Found m/z: (+) 367 (M+1)⁺; (−), 365 (M−1)⁻.

Example 1-1-4: 7-(3-Carboxypropyl)amino-3-(benzothiazol-2-yl)coumarin

Step A: 7-[3-(t-Butyloxycarbonyl)propyl]amino-3-(benzothiazol-2-yl)coumarin

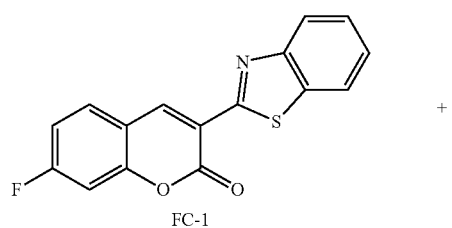

FC-1

Chemical Formula: C₁₆H₈FNO₂S
Molecular Weight: 297.30

+

3-(Benzothiazol-2-yl)-7-fluoro-coumarin (FC-1, 0.6 g, 2.02 mmol, 1 eqv) and t-butyl 4-aminobutanoate hydrochloride (AC-C3, 0.5 g, 2.56 mmol, 1.27 eqv) were added to anhydrous dimethyl sulfoxide (DMSO, 5 mL). After the addition was complete, the mixture was stirred for a few minutes at room temperature and then DIPEA (0.65 g, 5 mmol, 4 eqv) was added. The reaction mixture was stirred for 3 hours at temperature 100° C. After standing at room temperature for 1 hour, the yellow semi-solid reaction mixture was diluted with water (10 mL) and was left stirring overnight. The resulting precipitate was collected by suction filtration. Yield 0.7 g (79%). Purity, structure and composition were confirmed by HPLC, NMR and LCMS. MS (DUIS): MW Calculated 436.53. Found m/z: (+) 437 (M+1)⁺; (−), 435 (M−1)⁻.

I-1-4tBu

Chemical Formula: C₂₄H₂₄N₂O₄S
Molecular Weight: 436.53

Step B

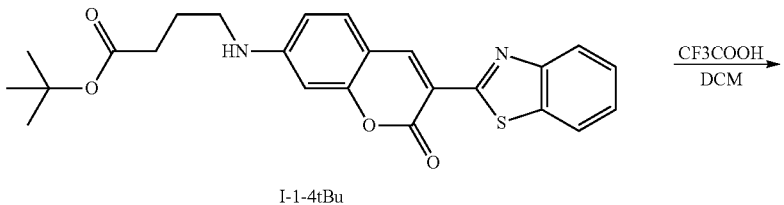

I-1-4tBu

Chemical Formula: C₂₄H₂₄N₂O₄S
Molecular Weight: 436.53

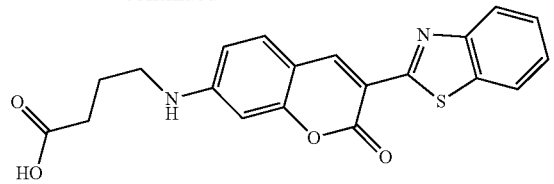

I-1-4

Chemical Formula: C$_{20}$H$_{16}$N$_2$O$_4$S
Molecular Weight: 380.42

A solution of 7-[3-(t-Butyloxycarbonyl)propyl]amino-3-(benzothiazol-2-yl)coumarin (I-1-4tBu, 0.7 g, 1.604 mmol) in anhydrous dichloromethane (25 mL) was treated with trifluoroacetic acid (1 mL) and the reaction mixture was stirred for 24 hours at room temperature. The solvents were distilled off and the residue was triturated with water (10 mL). The resulting precipitate was collected by suction filtration. Yield 0.59 g (97%). Purity, structure and composition were confirmed by HPLC, NMR and LCMS. MS (DUIS): MW Calculated 366.39. Found m/z: (+) 381 (M+1)$^+$; (−), 379 (M−1)$^−$. $^1$H NMR (400 MHz, DMSO-d$_6$) δ: 12.17 (s, 1H), 9.01 (s, 1H), 8.12 (d, J=8.0 Hz, 1H), 7.99 (d, J=8.1 Hz, 1H), 7.71 (d, J=8.8 Hz, 1H), 7.48-7.30 (m, 2H), 6.73 (dd, J=8.8, 2.1 Hz, 1H), 6.57 (d, J=2.1 Hz, 1H), 3.21 (q, J=6.6 Hz, 2H), 2.36 (d, J=7.3 Hz, 2H), 1.80 (p, J=7.3 Hz, 2H).

Example 1-1-5: 7-(5-Carboxypentyl)amino-3-(5-chloro-benzoxazol-2-yl)coumarin

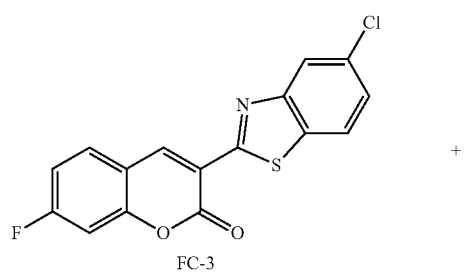

FC-3

Chemical Formula: C$_{16}$H$_7$ClFNO$_3$
Molecular Weight: 315.68

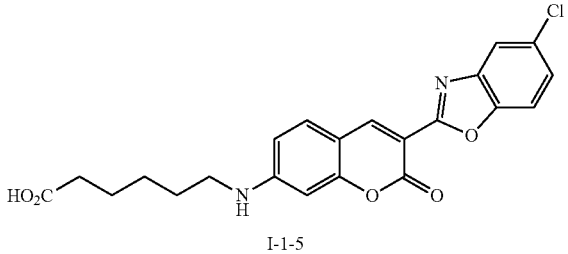

I-1-5

Chemical Formula: C$_{22}$H$_{19}$ClN$_2$O$_5$
Molecular Weight: 426.85

3-(5-Chloro-benzoxazol-2-yl)-7-fluoro-coumarin (FC-3, 0.32 g, 1 mmol, 1 eqv) and 6-aminohexanoic acid (AC-05, 0.26 g, 2 mmol, 2 eqv) were added to anhydrous dimethyl sulfoxide (DMSO, 5 mL) in round bottomed flask. After the addition was complete, the mixture was stirred for a few minutes at room temperature and then DIPEA (0.52 g, 4 mmol, 2 eqv) was added. The reaction mixture was stirred for 7 hours at temperature 135° C. Additional portions of 6-aminohexanoic acid (AC-1, 0.13 g, 1 mmol, 1 eqv) and DIPEA (0.26 g, 2 mmol, 2 eqv) were added and heating was continued at 135° C. for 5 hours. After standing at room temperature for 1 hour, the pale-yellow reaction mixture was diluted with water (15 mL) and was stirred overnight. The resulting precipitate was collected by suction filtration. Yield 0.09 g (21%). Purity, structure and composition of the product were confirmed by HPLC, NMR and LCMS. MS (DUIS): MW Calculated 426.10. Found m/z: (+) 427 (M+1)$^+$; (−) 425 (M−1)$^−$, 851 (2M−1)$^−$.

Example 2: 7-(5-Carboxypentyl)amino-3-(benzothiazol-2-yl)coumarin-6-sulfonic acid (2A) and 7-(5-Carboxypentyl)amino-3-(benzothiazol-2-yl)coumarin-8-sulfonic acid (2B)

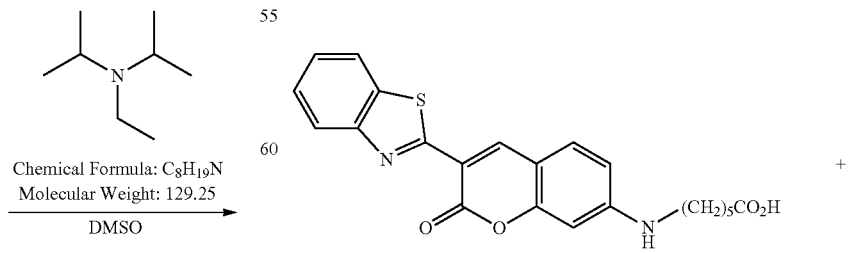

AC-C5

Chemical Formula: C$_6$H$_{13}$NO$_2$
Molecular Weight: 131.18

Chemical Formula: C$_8$H$_{19}$N
Molecular Weight: 129.25
DMSO

Chemical Formula: C$_{22}$H$_{20}$N$_2$O$_4$S
Molecular Weight: 408.47

-continued

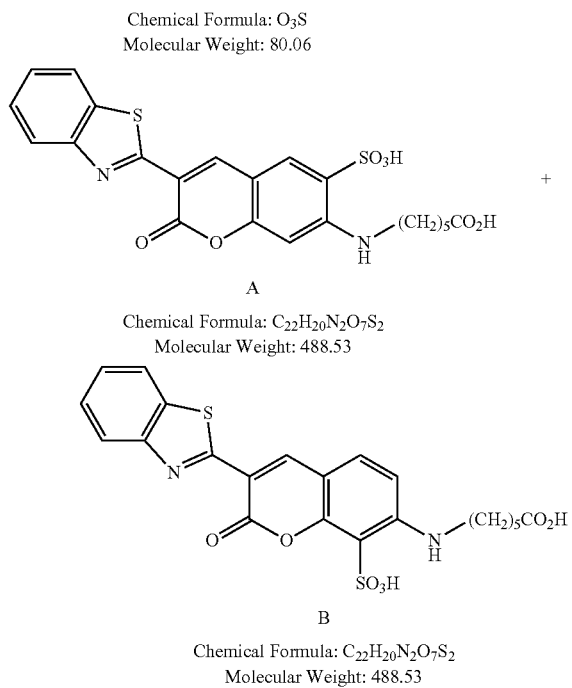

A

Chemical Formula: $C_{22}H_{20}N_2O_7S_2$
Molecular Weight: 488.53

B

Chemical Formula: $C_{22}H_{20}N_2O_7S_2$
Molecular Weight: 488.53

Compound I-1-1 (0.1 g, 0.245 mmol) was added in small portions with stirring to 20% fuming sulfuric acid (1 mL) that was cooled in a dry-ice/acetone bath. After the addition was complete, the mixture was stirred for 1 hour at 0° C., warmed to room temperature, and then stirred for 2 hours at room temperature. The solution was poured into anhydrous ether (25 mL). After standing at room temperature for 1 hour, the resulting precipitate was collected by suction filtration. Yield 78 mg (65%). $^1$H NMR (d$_6$-DMSO) showed compound 2A plus a small amount (~4%) of compound 2B.

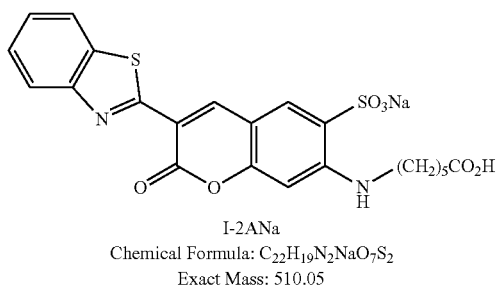

I-2ANa
Chemical Formula: $C_{22}H_{19}N_2NaO_7S_2$
Exact Mass: 510.05

Example 2A, Sodium Salt: The precipitate from above was resuspended in water (2 mL) and the pH of the suspension was adjusted to ~5 by addition of 5 M NaOH solution. The resulting mixture was poured into 10 mL of methanol and the suspension was filtered. The filtrate was evaporated to dryness to give the dye as sodium salt (I-2A-Na). Purity, structure and composition were confirmed by HPLC, NMR and LCMS. MS (DUIS): MW Calculated 488.07. Found m/z: (+) 489 (M+1)$^+$; (−) 243 (M−1)$^{2-}$, 487 (M−1)$^-$.

Preparation of Triethylammonium Salts of 2A and 2B: Compound I-1-1 (0.41 g, 1 mmol) was added in small portions with stirring to 20% fuming sulfuric acid (5 mL) that was cooled in a dry-ice/acetone bath. After the addition was complete, the mixture was stirred for 1 hour at 0° C., warmed to room temperature, and then stirred for 2 hours at room temperature. The solution was poured into anhydrous ether (50 mL). After standing at room temperature for 1 hour, the organic solvent layer is decanted and the semi-solid bottom layer was dissolved in acetonitrile-water (1:1, 10 mL). The pH of the solution was adjusted to ~7.0 by addition of 2 M TEAB solution in water. The resulting solution was filtered through a 20 μm Nylon filter and the isomers were separated by preparative HPLC. The solution of the isomers were concentrated in vacuo then re-dissolved in water (20 μL) and solvent removed in vacuo to dryness to give the dyes as triethylammonium salts. Purity and composition were confirmed by HPLC and LCMS.

Example 3: 7-(5-Carboxypentyl)amino-3-[5-sulfonato(benzothiazol-2-yl)-coumarin-6-sulfonate triethylammonium salt

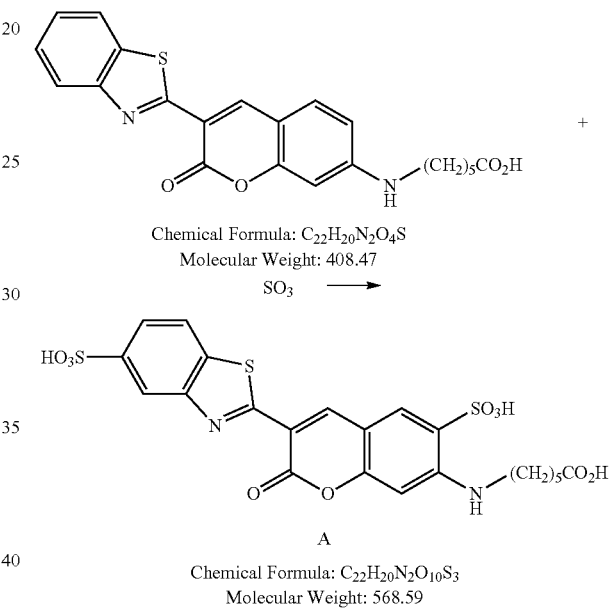

A

Chemical Formula: $C_{22}H_{20}N_2O_{10}S_3$
Molecular Weight: 568.59

Compound I-1-1 (0.08 g, 0.2 mmol) was added in small portions with stirring to 20% fuming sulfuric acid (2 mL) that was cooled in a dry-ice/acetone bath. After the addition was complete, the mixture was stirred for 1 hour at 0° C., warmed to room temperature, and then stirred for 2 hours at 70° C. The mixture was then stirred overnight at room temperature. The solution was poured into anhydrous ether (30 mL). After stirring at room temperature for 1 hour, the resulting precipitate was collected by suction filtration. Yield 43 mg (38%).

The precipitate was resuspended in water (2 mL) and the pH of the suspension was adjusted to ~7.5 by addition of 2 M TEAB solution in water. The resulting mixture was filtered through a 20 μm Nylon filter and purified by preparative HPLC. The dye fraction was concentrated in vacuo then re-dissolved in water (20 μL) and solvent removed in vacuo to dryness to give the dye as the bis-triethylammonium salt. Purity and composition were confirmed by HPLC and LCMS. MS (DUIS): MW Calculated 568.03. Found m/z: (+) 569 (M+1)$^+$.

Fluorescence intensities of exemplary dye solutions were compared with a commercial dye for the same spectral region. The results are shown in Table 2 and demonstrate significant advantages of the exemplary dyes for fluorescence based analytical applications.

TABLE 2

Spectral properties of the new fluorescent dyes disclosed in the examples

| Number | Structure | Abs. max nm | Fluorescence max nm | Relative Fluor.* Intensity, % |
|---|---|---|---|---|
| I-1-1 | benzothiazole-coumarin-NH(CH$_2$)$_5$CO$_2$H | 460 | 499 | 275 |
| I-1-2 | benzimidazole-coumarin-NH(CH$_2$)$_5$CO$_2$H | 437 | 488 | 175 |
| I-1-3 | benzothiazole-coumarin-NH(CH$_2$)$_2$CO$_2$H | 453 | 499 | 230 |
| I-1-4 | benzothiazole-coumarin-NH(CH$_2$)$_3$CO$_2$H | 455 | 500 | 220 |
| I-1-5 | Cl-benzoxazole-coumarin-NH(CH$_2$)$_5$CO$_2$H | 430 | 490 | 200 |
| I-2A | benzothiazole-coumarin(SO$_3$H)-NH(CH$_2$)$_5$CO$_2$H | 465 | 503 | 395 |

TABLE 2-continued

Spectral properties of the new fluorescent dyes disclosed in the examples

| Number | Structure | Abs. max nm | Fluorescence max nm | Relative Fluor.* Intensity, % |
|---|---|---|---|---|
| I-2B | (benzothiazole-coumarin with NH⁺(C₂H₅)₃, NH(CH₂)₅CO₂H, SO₃⁻ substituents) | 466 | 505 | 280 |
| I-3 | (sulfonated benzothiazole-coumarin with 2 NH⁺(C₂H₅)₃, SO₃⁻, NH(CH₂)₅CO₂H substituents) | 472 | 515 | 330 |
| Standard | Atto465 from AttoTec | 455 | 508 | 100 |

*Excitation of fluorescence @ 460 nm

Example 4: General Procedure for the Synthesis of Fully Functional Nucleotide Conjugates with New Fluorescent Dyes Coumarin fluorescent dyes disclosed herein were coupled with appropriate amino-substituted adenine (A) and cytosine (C) nucleotide derivatives A-LN3-NH$_2$ or C-LN3-NH$_2$:

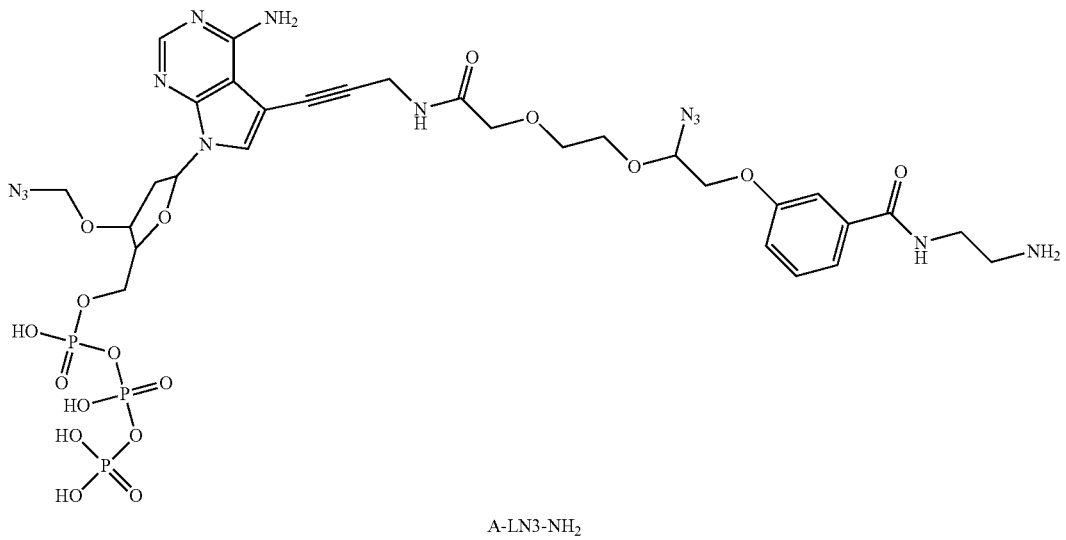

A-LN3-NH$_2$

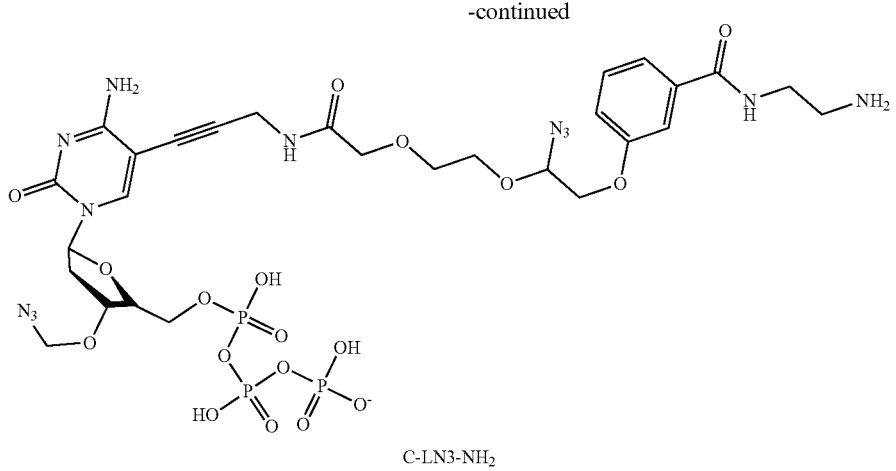
C-LN3-NH₂
after activation of carboxylic group of a dye with appropriate reagents according to the following adenine exemplary scheme:
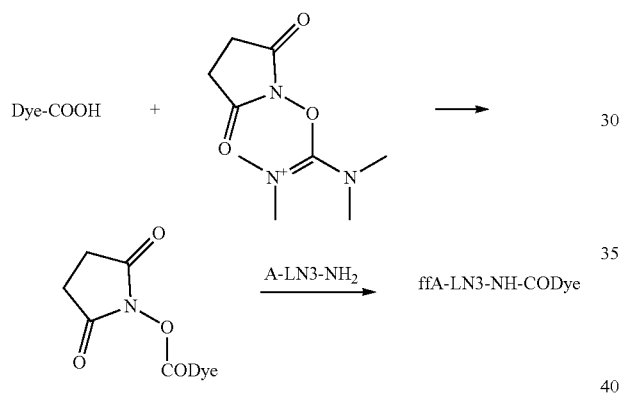
The general product for the adenine coupling is as shown below:
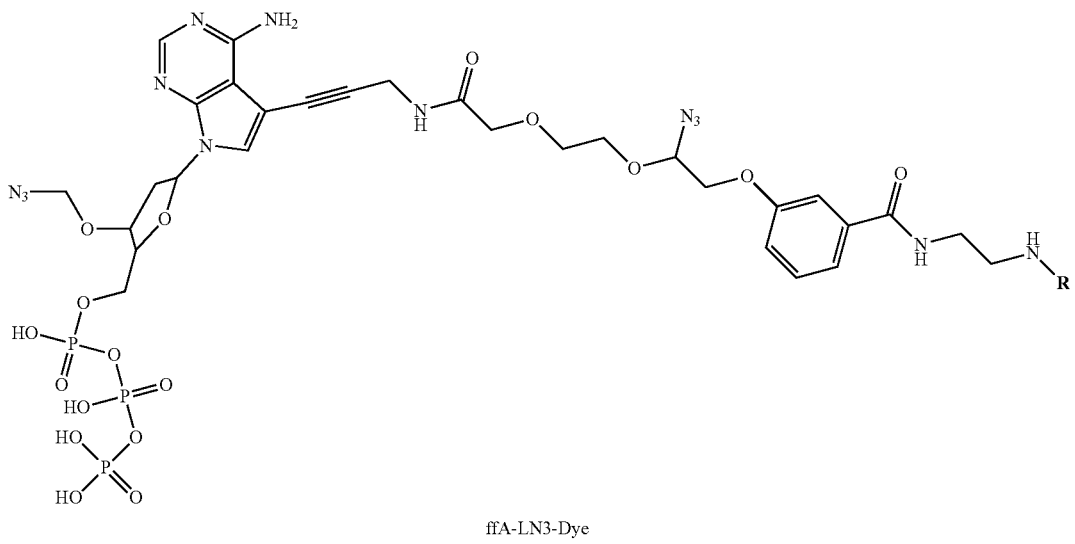
ffA-LN3-Dye ffA-LN3-Dye refers to a fully functionalized A nucleotide with an LN3 linker and labeled with a coumarin dye disclosed herein. The R group in each of the structures refers to the coumarin dye moiety after conjugation.

The dye (10 μmol) is dried by placing into a 5 mL round-bottomed flask and is dissolved in anhydrous dimethylformamide (DMF, 1 mL) then the solvent is distilled off in vacuo. This procedure is repeated twice. The dried dye is dissolved in anhydrous N,N-dimethylacetamide (DMA, 0.2 mL) at room temperature. N,N,N',N'-Tetramethyl-O—(N-succinimidyl)uronium tetrafluoroborate (TSTU, 1.5 eq., 15 μmol, 4.5 mg) is added to the dye solution, then DIPEA (3 eq., 30 μmol, 3.8 mg, 5.2 μL) is added via micropipette to this solution. The reaction flask is sealed under nitrogen gas. The reaction progress is monitored by TLC (eluent Acetonitrile-Water 1:9) and HPLC. Meanwhile, a solution of the appropriate amino-substituted nucleotide derivative (A-LN3-NH$_2$, 20 mM, 1.5 eq, 15 μmol, 0.75 mL) is concentrated in vacuo then re-dissolved in water (20 μL). A solution of the activated dye in DMA is transferred to the flask containing the solution of N-LN3-NH$_2$. More DIPEA (3 eq, 30 μmol, 3.8 mg, 5.2 μL) is added along with triethylamine (1 μL). Progress of coupling is monitored hourly by TLC, HPLC, and LCMS. When the reaction is complete, triethylamine bicarbonate buffer (TEAB, 0.05 M~3 mL) is added to the reaction mixture via pipette. Initial purification of the fully functionalized nucleotide is carried out by running the quenched reaction mixture through a DEAE-Sephadex® column to remove most of remaining unreacted dye. For example, Sephadex is poured into an empty 25 g Biotage cartridge, solvent system TEAB/MeCN. The solution from the Sephadex column is concentrated in vacuo. The remaining material is re-dissolved in the minimum volume of water and acetonitrile, before filtering through a 20 μm Nylon filter. The filtered solution is purified by preparative-HPLC. The composition of prepared compounds was confirmed by LCMS.

TABLE 3

Structure and spectral properties of various nucleotides labeled with new coumarin based dyes disclosed herein.

| | Spectral properties in SRE | | |
|---|---|---|---|
| Compd. | Absorption, nm | Fluorescence, nm | Relative Fluor. Intensity, % |
| ffA-I-1-1 | 448 | 505 | 480 |
| ffA-I-1-3 | 454 | 499 | 500 |
| ffA-I-2A | 475 | 510 | 575 |
| ffA-Standard | 465 | 504 | 100 |

A comparison of fluorescence intensities in solution of nucleotides labeled with dyes disclosed herein with appropriate data for nucleotides labeled with the a commercial dye for the same spectral region (Atto465 from AttoTec GmbH) demonstrate the advantage of the dyes described herein for labeling of biomolecules to use in fluorescence based analytical applications.

Example 5: Sequencing Analysis

Figure 1B:
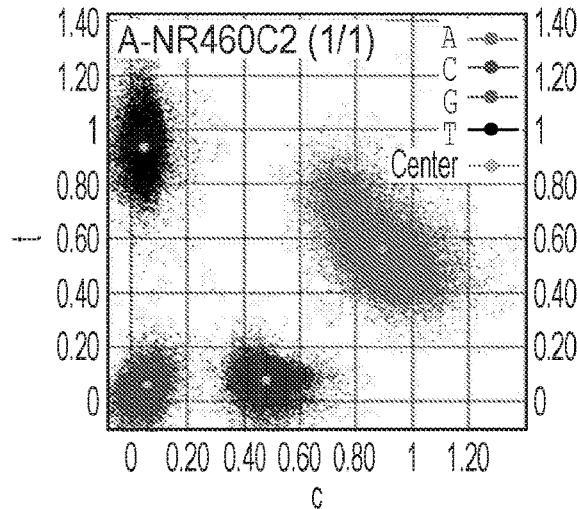
Figure 1C:
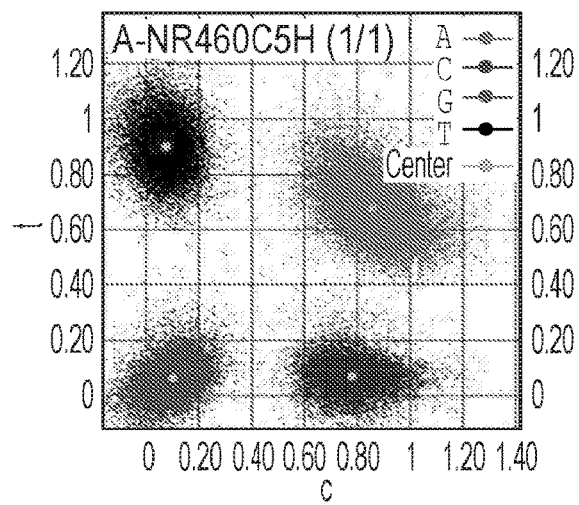

FfA's based on dyes disclosed herein were used in sequencing on an Illumina sequencer using sequencing-by-synthesis chemistry and the images in FIGS. 1A, 1B, and 1C demonstrate their utility. Scan temp 22° C., Expose times: blue 500 ms, green 500 ms; SFA flow cell. The numbers in bracket in the charts below indicate the ratio of new blue ffA to greenA. The A, C, G, and T nucleotides were labeled as follows: A: Ex 2A (FIG. 1A), Ex I-1-3 (FIG. 1B), and Ex I-1-1 (FIG. 1C); C: NR440; G: Dark; and T: AF550POPOS0.
NR440 (See WO2018/060482) AF550POPOS0 (See WO2017/051201)

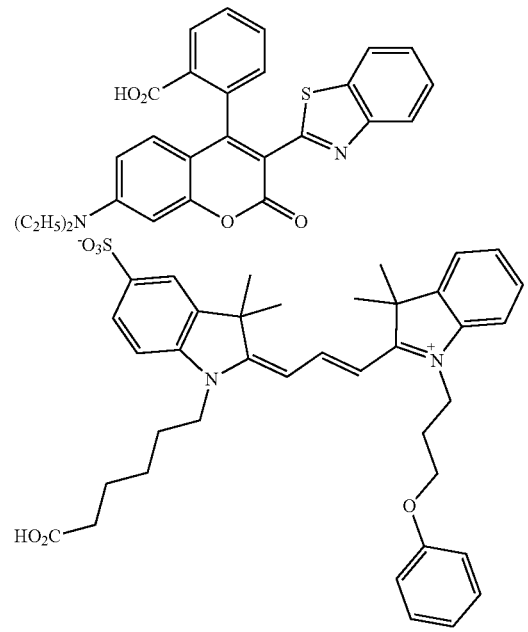

What is claimed is:

1. A nucleotide labeled with a compound of Formula (II) or a salt thereof:

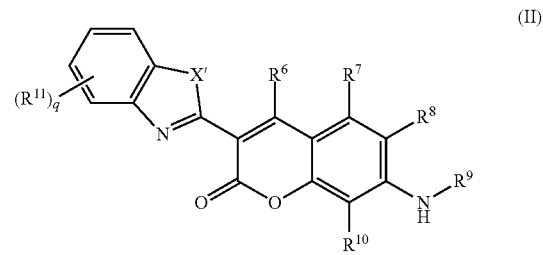

wherein:
X' is selected from O, S, and NR$^p$, where R' is H or C$_{1-6}$alkyl;
R$^6$ is H or C$_{1-4}$alkyl;
R$^7$ is H, halo, —CN, —OH, optionally substituted C$_{1-4}$alkyl, optionally substituted C$_{1-4}$alkenyl, optionally substituted C$_{2-4}$alkynyl, —CO$_2$H, —SO$_3$H, —SO$_2$NH$_2$, —SO$_2$NH(C$_{1-4}$alkyl), —SO$_2$N(C$_{1-4}$alkyl)$_2$, and optionally substituted C$_{1-4}$alkoxy;
R$^8$ and R$^{10}$ are each independently H, halo, —CN, —CO$_2$H, amino, —OH, —SO$_3$H, —SO$_2$NH$_2$, —SO$_2$NH(C$_{1-4}$alkyl), —SO$_2$N(C$_{1-4}$alkyl)$_2$, optionally substituted C$_{1-6}$alkyl, optionally substituted C$_{1-6}$alkenyl, optionally substituted C$_{2-6}$alkynyl, or optionally substituted C$_{1-6}$alkoxy;
R$^9$ is C$_{2-6}$alkyl substituted with —CO$_2$H, —CO$_2$C$_{1-4}$alkyl, —CONH$_2$, —CONH(C$_{1-4}$alkyl), —CON(C$_{1-4}$alkyl)$_2$, —CN, —SO$_3$H, —SO$_2$NH$_2$, —SO$_2$NH(C$_{1-4}$alkyl), or —SO$_2$N(C$_{1-4}$alkyl)$_2$;

each R$^{11}$ is independently halo, —CN, carboxy, amino, —OH, C-amido, N-amido, nitro, —SO$_3$H, —SO$_2$NH$_2$, —SO$_2$NH(C$_{1-4}$alkyl), —SO$_2$N(C$_{1-4}$alkyl)$_2$, optionally substituted alkyl, optionally substituted alkenyl, optionally substituted alkynyl, and optionally substituted C$_{1-6}$alkoxy; and q is 0, 1, or 2.

2. The labeled nucleotide of claim 1, wherein the compound is attached to the nucleotide at the R$^9$ position.

3. The labeled nucleotide of claim 2, wherein R$^9$ is C$_{2-6}$alkyl substituted with —CO$_2$H, and the attachment forms an amide bond using the —CO$_2$H group.

4. The labeled nucleotide of claim 3, wherein the compound is attached to the C5 position of a pyrimidine base or the C7 position of a 7-deaza purine base of the nucleotide through a linker moiety.

5. The labeled nucleotide of claim 4, further comprising a 3' blocking group covalently attached to the ribose or 2-deoxyribose sugar of the nucleotide.

6. The labeled nucleotide of claim 1, wherein X' is O or S.

7. The labeled nucleotide of claim 1, wherein each of R$^6$ and R$^7$ is H.

8. The labeled nucleotide of claim 1, wherein each of R$^8$ and R$^{10}$ is independently H, —SO$_3$H, or —SO$_2$NH$_2$.

9. An oligonucleotide or polynucleotide incorporating a labeled nucleotide according to claim 1.

10. A kit comprising a first type of labeled nucleotide according to claim 1.

11. The kit of claim 10, wherein the kit comprises four types of nucleotides, wherein each type of nucleotide carries a label having a distinct absorbance maximum that is distinguishable from the other labels.

12. The kit of claim 10, wherein the kit comprises four types of nucleotides, wherein a second type of nucleotide carries a second label, a third type of nucleotide carries a third label, and a fourth type of nucleotide is unlabeled (dark).

13. The kit of claim 10, wherein the kit comprises four types of nucleotides, wherein a second type nucleotide carries a second label, a third type of nucleotide carries a mixture of two labels, and a fourth type of nucleotide is unlabeled (dark).

14. A method of sequencing different template polynucleotides, comprising:
(a) incorporating one or more different types of nucleotides to the template polynucleotides, wherein each type of nucleotide comprises a 3' blocking group covalently attached to a 2-deoxyribose sugar of the nucleotide, and one type of nucleotide is the labeled nucleotide according to claim 5; and
(b) imaging and detecting the fluorescent signal from the nucleotides incorporated into the template polynucleotides.

15. The method of claim 14, wherein X' is O or S.

16. The method of claim 14, wherein each of R$^6$ and R$^7$ is H.

17. The method of claim 14, wherein each of R$^8$ and R$^{10}$ is independently H, —SO$_3$H, or —SO$_2$NH$_2$.

18. The method of claim 14, wherein the sequencing is performed on an automated sequencing instrument.

19. The method of claim 18, wherein the automated sequencing instrument comprises two light sources operating at different wavelengths.

20. The method of claim 19, wherein one light has a wavelength from about 450 nm to about 460 nm.

* * * * *